(12) United States Patent
Chu et al.

(10) Patent No.: US 8,871,069 B2
(45) Date of Patent: Oct. 28, 2014

(54) LOW TOTAL SALT REAGENT COMPOSITIONS AND SYSTEMS FOR BIOSENSORS

(75) Inventors: Amy H. Chu, Elkhart, IN (US); Huan-Ping Wu, Granger, IN (US); Boru Zhu, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 418 days.

(21) Appl. No.: 13/154,088

(22) Filed: Jun. 6, 2011

(65) Prior Publication Data

US 2011/0297540 A1    Dec. 8, 2011

Related U.S. Application Data

(63) Continuation of application No. PCT/US2009/066963, filed on Dec. 7, 2009.

(60) Provisional application No. 61/201,242, filed on Dec. 8, 2008.

(51) Int. Cl.
| | | |
|---|---|---|
| *G01N 27/327* | (2006.01) | |
| *G01N 33/543* | (2006.01) | |
| *C12Q 1/00* | (2006.01) | |

(52) U.S. Cl.
CPC ............ *C12Q 1/004* (2013.01); *G01N 33/5438* (2013.01)
USPC .................................................... 204/403.04

(58) Field of Classification Search
CPC ........................ G01N 27/3273; G01N 27/3274
USPC ........................ 204/403.01–403.15
See application file for complete search history.

(56) References Cited

U.S. PATENT DOCUMENTS

| | | | |
|---|---|---|---|
| 5,120,420 A | 6/1992 | Nankai et al. | |
| 5,393,615 A | 2/1995 | Corey et al. | |

(Continued)

FOREIGN PATENT DOCUMENTS

| | | |
|---|---|---|
| WO | 2004113902 | 12/2004 |
| WO | 2004113917 | 12/2004 |

(Continued)

OTHER PUBLICATIONS

International Searching Authority, "International Search Report and Written Opinion for PCT/20091066963", Mar. 22, 2010, Publisher: European Patent Office, Published in: EP.

(Continued)

*Primary Examiner* — J. Christopher Ball
(74) *Attorney, Agent, or Firm* — Blanchard & Associates

(57) ABSTRACT

A biosensor system for determining the concentration of an analyte in a sample is disclosed that includes a reaction means for selectively performing a redox reaction of an analyte, and a measurement means for measuring a rate of the redox reaction of the analyte. The reaction means includes a binder, a buffer salt, a mediator including at most 20% (w/w) of an inorganic, non-transition metal salt, and an enzyme system. The measurement means includes at least two conductors. The measurement means measures an output signal value from the reaction means at a maximum kinetic performance within at most 7 seconds of introducing a sample to the reaction means, where the output signal value is responsive to the concentration of the analyte in the sample, and the measurement means determines at least one ΔS value responsive to at least one error parameter. The measurement means further determines the analyte concentration in the sample from a compensation equation including at least one reference correlation and the at least one ΔS value, where the compensation equation has a $R^2$ value of at least 0.5.

43 Claims, 8 Drawing Sheets

(56) References Cited

U.S. PATENT DOCUMENTS

| | | |
|---|---|---|
| 5,498,542 A | 3/1996 | Corey et al. |
| 5,508,171 A | 4/1996 | Walling et al. |
| 5,520,786 A | 5/1996 | Bloczynski et al. |
| 5,798,031 A | 8/1998 | Charlton et al. |
| 6,153,069 A | 11/2000 | Pottgen et al. |
| 6,531,040 B2 | 3/2003 | Musho et al. |
| 6,645,368 B1 * | 11/2003 | Beaty et al. .................. 205/792 |
| 7,163,616 B2 | 1/2007 | Vreeke et al. |
| 7,326,539 B2 | 2/2008 | Fromherz et al. |
| 7,862,696 B2 | 1/2011 | Wu et al. |
| 8,147,674 B2 | 4/2012 | Wu |
| 8,262,899 B2 | 9/2012 | Wu |
| 2008/0173552 A1 | 7/2008 | Wu et al. |
| 2008/0179197 A1 | 7/2008 | Wu |
| 2009/0095625 A1 * | 4/2009 | Forrow .................. 204/403.14 |
| 2009/0145756 A1 | 6/2009 | Zhu et al. |
| 2011/0297554 A1 | 12/2011 | Wu et al. |

FOREIGN PATENT DOCUMENTS

| | | |
|---|---|---|
| WO | 2008036516 | 3/2008 |
| WO | 2009076402 | 6/2009 |
| WO | 2009076433 | 6/2009 |
| WO | 2009108239 | 9/2009 |

OTHER PUBLICATIONS

Wikipedia, "Coefficient of Determination", "Wikipedia, the free encyclopedia", Jan. 15, 2014, Publisher: www.wikipedia.com.

* cited by examiner

LOW TOTAL SALT REAGENT COMPOSITIONS AND SYSTEMS FOR BIOSENSORS

REFERENCE TO RELATED APPLICATIONS

This application is a continuation of PCT Application No. PCT/US2009/066963 entitled "Low Total Salt Reagent Compositions And Systems For Biosensors" filed Dec. 7, 2009, which claims the benefit of U.S. Provisional Application No. 61/201,242 entitled "Low-Salt Reagent Composition" filed Dec. 8, 2008, which are incorporated by reference in their entirety.

BACKGROUND

Biosensors provide an analysis of a biological fluid, such as whole blood, serum, plasma, urine, saliva, interstitial, or intracellular fluid. Typically, biosensors have a measurement device that analyzes a sample residing in a test sensor. The sample usually is in liquid form and may be a biological fluid or a derivative of a biological fluid, such as an extract, a dilution, a filtrate, or a reconstituted precipitate. The analysis performed by the biosensor determines the presence and/or concentration of one or more analytes in the biological fluid. Examples of analytes include alcohol, glucose, uric acid, lactate, cholesterol, bilirubin, free fatty acids, triglycerides, proteins, ketones, phenylalanine, or enzymes. The analysis may be useful in the diagnosis and treatment of physiological abnormalities. For example, a diabetic individual may use a biosensor to determine the glucose level in whole blood, and this information may be used in adjusting the individual's diet and/or medication.

Biosensors may be designed to analyze one or more analytes and may use different sample volumes. Some biosensors may analyze a single drop of whole blood, such as from 0.25-15 microliters (µL) in volume. Biosensors may be implemented using bench-top, portable, and like measurement devices. Portable measurement devices may be hand-held and allow for the identification and/or quantification of one or more analytes in a sample. Examples of portable measurement devices include the Ascensia Breeze® and Elite® meters of Bayer HealthCare in Tarrytown, N.Y., while examples of bench-top measurement devices include the Electrochemical Workstation available from CH Instruments in Austin, Tex. Biosensors providing shorter analysis times, while supplying the desired accuracy and/or precision, provide a substantial benefit to the user.

In electrochemical biosensors, the analyte concentration is determined from an electrical signal generated by an oxidation/reduction or redox reaction of the analyte, or of a species responsive to the analyte, when an input signal is applied to the sample. The input signal may be applied as a single electrical pulse or in multiple pulses, sequences, or cycles. An oxidoreductase, such as an enzyme or similar species, may be added to the sample to enhance the electron transfer from a first species to a second species during the redox reaction. The enzyme or similar species may react with a single analyte, thus providing specificity to a portion of the generated output signal.

Electrochemical biosensors usually include a measurement device having electrical contacts that connect with electrical conductors in the test sensor. The test sensor may be adapted for use outside, inside, or partially inside a living organism. When used outside a living organism, a sample of the biological fluid is introduced into a sample reservoir in the test sensor. The test sensor may be placed in the measurement device before, after, or during the introduction of the sample for analysis. When inside or partially inside a living organism, the test sensor may be continually immersed in the sample, or the sample may be intermittently introduced to the test sensor. The test sensor may include a reservoir that partially isolates a volume of the sample, or the test sensor may be open to the sample. Similarly, the sample may continuously flow through the test sensor or be interrupted for analysis.

For electrochemical biosensors, the conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The test sensor may be formed by disposing or printing electrodes on an insulating substrate using multiple techniques, such as those described in U.S. Pat. Nos. 6,531,040; 5,798,031; and 5,120,420. The electrodes may be formed by disposing one or more reagent composition on one or more of the conductors. More than one of the conductors may be coated by the same reagent composition, such as when the working and counter electrodes are coated by the same composition. Multiple techniques known to those of ordinary skill in the art may be used to dispose the reagent composition on the test sensor. The reagent composition may be disposed on the conductors as a reagent fluid and then dried. When the sample is introduced to the test sensor, the reagent composition begins to rehydrate.

Different reagent compositions may be disposed on the conductors. Thus, the reagent composition of the working electrode may contain the enzyme, the mediator, and a binder while the reagent composition of the counter electrode contains a mediator, which could be the same as or different from the mediator of the working electrode, and a binder. The reagent composition may include an ionizing agent for facilitating the oxidation or reduction of the analyte, such as an oxidoreductase, as well as any mediators or other substances that assist in transferring electrons between the analyte and the working electrode. In addition to binding the reagents together, the binder may assist in filtering red blood cells, preventing them from coating the conductor surface, and stabilizing the oxidoreductase, for example.

The sooner an output signal is obtained from the test sensor, where the concentration of the analyte may be determined accurately from the output signal, the sooner the analysis may be completed. Thus, biosensors including reagent compositions providing shorter analysis times, while supplying the desired accuracy and/or precision, may provide a substantial benefit to the user.

The measurement performance of a biosensor system is defined in terms of accuracy and/or precision. Increases in accuracy and/or precision provide for an improvement in measurement performance of the system. Accuracy may be expressed in terms of bias of the sensor system's analyte reading in comparison to a reference analyte reading, with larger bias values representing less accuracy. Precision may be expressed in terms of the spread or variance of the bias among multiple analyte readings in relation to a mean. Bias is the difference between one or more values determined from the biosensor system and one or more accepted reference values for the analyte concentration in the biological fluid. Thus, one or more errors in the measured analysis results in the bias of the determined analyte concentration of a biosensor system. Bias may be expressed in terms of "absolute bias" or "percent bias". Absolute bias may be expressed in the units of the measurement, such as mg/dL, while percent bias may be expressed as a percentage of the absolute bias value over the reference value. Accepted reference values may be obtained with a reference instrument, such as the YSI 2300 STAT PLUS™ available from YSI Inc., Yellow Springs, Ohio.

Biosensor systems may provide an output signal during the analysis of the biological fluid that includes one or multiple errors. These errors may be reflected in an abnormal output signal, such as when one or more portions or the entire output signal is non-responsive or improperly responsive to the analyte concentration of the sample. These errors may be from one or more contributors, such as the physical characteristics of the sample, the environmental aspects of the sample, the operating conditions of the system, interfering substances, and the like. Physical characteristics of the sample include hematocrit (red blood cell) concentration and the like. Environmental aspects of the sample include temperature and the like. Operating conditions of the system include underfill conditions when the sample size is not large enough, slow-filling of the sample, intermittent electrical contact between the sample and one or more electrodes in the test sensor, degradation of the reagents that interact with the analyte, and the like. Interfering substances include ascorbic acid, uric acid, acetaminophen, and the like. There may be other contributors or a combination of contributors that cause errors.

Many biosensor systems include one or more methods to correct errors associated with an analysis. The concentration values obtained from an analysis with an error may be inaccurate. Thus, the ability to correct these inaccurate analyses may increase the accuracy of the concentration values obtained. An error correction system may compensate for one or more errors, such as a sample temperature or sample hematocrit content, that is different from a reference temperature or reference hematocrit value. For example, conventional biosensor systems may be configured to report glucose concentrations presuming a 40% (v/v) hematocrit content for a whole blood sample, regardless of the actual hematocrit content of the sample. In these systems, any glucose measurement performed on a blood sample containing less or more than 40% hematocrit will include error and thus have bias attributable to the hematocrit effect.

Accordingly, there is an ongoing need for improved biosensor systems, especially those that may provide increasingly accurate and/or precise determination of the concentration of the analyte in the sample. Moreover, there is a need for improved biosensor systems that may provide increasingly shorter analysis times, while supplying the desired accuracy and/or precision. The systems, devices, and methods of the present invention overcome at least one of the disadvantages associated with conventional biosensor systems.

SUMMARY

A biosensor system for determining the concentration of an analyte in a sample is disclosed that includes a reaction means for selectively performing a redox reaction of an analyte, and a measurement means for measuring a rate of the redox reaction of the analyte. The reaction means includes a binder; a buffer salt; a mediator including at most 20% (w/w) of an inorganic, non-transition metal salt; and an enzyme system. The measurement means includes at least two conductors. The measurement means measures an output signal value from the reaction means at a maximum kinetic performance within at most 7 seconds of introducing a sample to the reaction means, where the output signal value is responsive to the concentration of the analyte in the sample, and the measurement means determines at least one $\Delta S$ value responsive to at least one error parameter. The measurement means further determines the analyte concentration in the sample from a compensation equation including at least one reference correlation and the at least one $\Delta S$ value, where the compensation equation has a $R^2$ value of at least 0.5.

A test sensor for determining the concentration of an analyte in a sample is disclosed that includes at least two conductors, where one of the conductors is a working electrode, and a reagent composition disposed on or near the working electrode. The reagent composition has an average reagent composition surface area and includes a binder; a buffer salt at a concentration of at most 9.54 nmol per $mm^2$ of the reagent composition surface area; a mediator at a concentration of at most 4.76 nmol per $mm^2$ of the reagent composition surface area, where the mediator includes at most 20% (w/w) of an inorganic, non-transition metal salt; an enzyme system; and a non-ionic surfactant.

A test sensor for determining the concentration of an analyte in a sample is disclosed that includes at least two conductors, where one of the conductors is a working electrode; a reservoir having a reservoir volume; and a reagent composition disposed on or near the working electrode. The reagent composition includes a binder; a buffer salt at a concentration of at most 67 nmol per μL of the reservoir volume; a mediator at a concentration of at most 40 nmol per μL of the reservoir volume, where the mediator includes at most 20% (w/w) of an inorganic, non-transition metal salt; an enzyme system; and a non-ionic surfactant.

A test sensor for determining the concentration of an analyte in a sample is disclosed that includes at least two conductors, where one of the conductors is a working electrode having a working electrode area, and a reagent composition disposed on or near the working electrode. The reagent composition includes a binder; a buffer salt at a concentration of at most 167 nmol per $mm^2$ of the working electrode area; a mediator at a concentration of at most 80 nmol per $mm^2$ of the working electrode area, where the mediator includes at most 20% (w/w) of an inorganic, non-transition metal salt; an enzyme system; and a non-ionic surfactant.

A method of determining the concentration of an analyte in a sample is disclosed that includes introducing an aqueous sample including at least one analyte to a reagent composition, rehydrating the reagent composition with the aqueous sample; applying an input signal between conductors, the sample providing electrical communication between the analyte, the reagent composition, and the conductors; and determining the concentration of one or more analytes in the sample from one or more output signal values, the output signal values measured from the conductors within at most 7 seconds of introducing the aqueous sample to the reagent composition. The reagent composition has an average reagent composition surface area and may include a binder; a buffer salt present at concentration of at most 9.54 nmol per $mm^2$ of the reagent composition surface area; a mediator present at a concentration of at most 4.76 nmol per $mm^2$ of the reagent composition surface area, where the mediator includes at most 20% (w/w) of an inorganic, non-transition metal salt; an enzyme system; and a non-ionic surfactant.

A method of determining the concentration of an analyte in a sample is disclosed that includes generating at least one output signal value responsive to the concentration of the analyte in the sample, determining at least one $\Delta S$ value from at least one error parameter, compensating the at least one output signal value with at least one reference correlation and at least one $\Delta S$ value, and determining the analyte concentration in the sample from the at least one output signal value.

A reagent fluid for forming reagent composition is disclosed that includes water; a binder; a buffer salt present at a concentration of at most 115 mM; a mediator present at a concentration of at most 90 mM, where the mediator includes at most 20% (w/w) of an inorganic, non-transition metal salt; an enzyme system; and a non-ionic surfactant. The fluid may have a pH from 4.5 to 7.5.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

A reagent composition for a test sensor is disclosed that includes a lower concentration of total salt than conventional reagent compositions for test sensors. The total concentration of salt in the low total salt reagent compositions, including buffer salt and inorganic, non-transition metal salt, may be half or less of the total concentration of the salts in a conventional sensor. The low total salt reagent compositions may include a non-ionic surfactant, and may further include an ionic surfactant.

The output signal from a test sensor that includes a low total salt reagent composition may be correlated accurately to the analyte concentration of whole blood samples over a wide range of hematocrit contents. This is a substantial improvement over conventional test sensors having higher concentrations of total salt in the reagent composition, which may provide accurate measurements over a more narrow range of hematocrit content.

The output signal from a test sensor that includes a low total salt reagent composition may be correlated accurately to the analyte concentration of a sample within about seven seconds. This is a substantial improvement over conventional test sensors having higher concentrations of total salt in the reagent composition, which may require more than seven seconds to provide an output signal for accurate correlation with the analyte concentration of the sample.

Figure 1A:
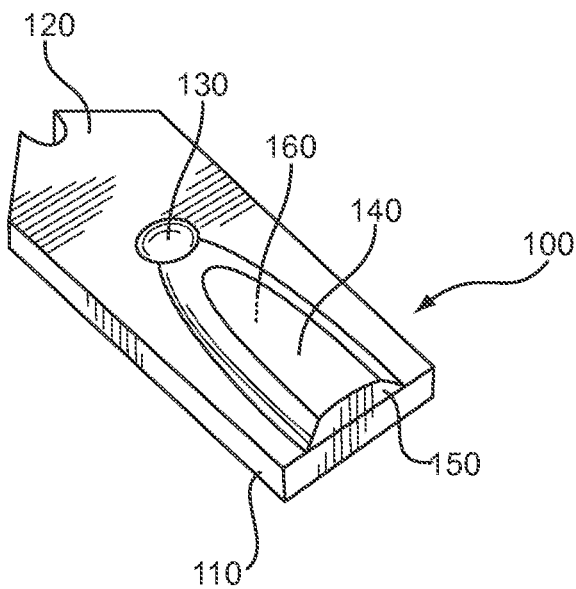
FIG. 1A is a perspective representation of an assembled test sensor.
Figure 1B:
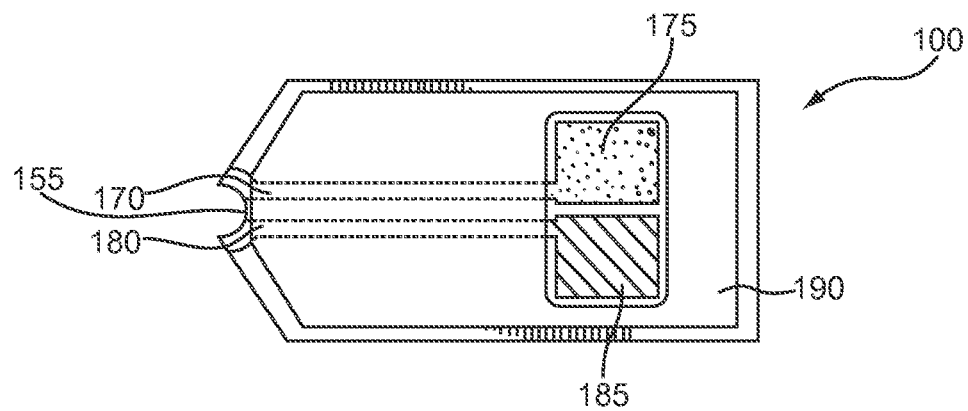
FIG. 1B is a top-view representation of the test sensor of FIG. 1A, with the lid removed.

FIGS. 1A and 1B depict a test sensor 100. FIG. 1A is a perspective representation of the assembled test sensor 100 including a sensor base 110 at least partially covered by a lid 120, and including a vent 130, a sample coverage area 140, and an input end opening 150. A partially-enclosed reservoir 160 is formed between the base 110 and the lid 120. Other test sensor designs also may be used.

A liquid sample for analysis may be transferred into the reservoir 160 by introducing the liquid to the opening 150. The liquid fills the reservoir 160 while expelling the previously contained air through the vent 130. The reservoir 160 may contain a retention composition (not shown) that assists in retaining the liquid sample in the reservoir. Examples of retention compositions include water-swellable polymers, such as carboxymethyl cellulose and polyethylene glycol; and porous polymer matrices, such as dextran and polyacrylamide.

FIG. 1B represents a top-view of the test sensor 100, with the lid 120 removed. Conductors 170 and 180 may run under a dielectric layer 190 from a measurement device interface 155 to a working electrode 175 and a counter electrode 185, respectively. The working and counter electrodes 175, 185 may be in substantially the same plane, as depicted in the figure, or in different planes (not shown). The working and counter electrodes 175, 185 may be separated from an upper portion of the lid 120 by at least 100 µm. The dielectric layer 190 may partially cover the electrodes 175, 185 and may be made from any suitable dielectric material, such as an insulating polymer.

The counter electrode 185 may support the electrochemical activity at the working electrode 175 of the test sensor 100. The potential to support the electrochemical activity at the working electrode 175 may be provided to the sensor system by forming the counter electrode 185 from an inert material, such as carbon, and including a soluble redox species, such as a ferricyanide mediator, within the reservoir 160. The potential at the counter electrode 185 may be a reference potential achieved by forming the counter electrode 185 from a redox pair, such as Ag/AgCl, to provide a combined reference-counter electrode. Alternatively, the test sensor 100 may be provided with a third conductor and electrode (not shown) to provide a reference potential to the sensor system.

The area of the working electrode 175 may be the same as the area of the counter electrode 185, or one of the electrodes may have a larger area than the other electrode. Presently, it is preferred that the working electrode area is smaller than the counter electrode area. Preferably the ratio of the counter electrode area to the working electrode area is at least 1, more preferably at least 1.1, more preferably at least 1.2, more preferably at least 1.3, more preferably at least 1.4, and more preferably at least 1.5.

Figure 2:
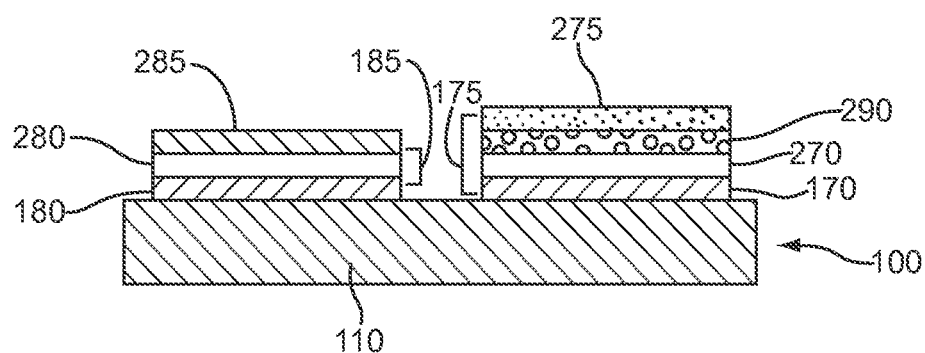
FIG. 2 is an end view representation of the test sensor of FIG. 1B.

FIG. 2 represents an end-view diagram of the test sensor of FIG. 1B showing the layer structures of the working electrode 175 and the counter electrode 185. The conductors 170 and 180 may be disposed directly on the base 110. Surface conductor layers 270 and 280 optionally may be disposed on the conductors 170 and 180, respectively. The surface conductor layers 270, 280 may be made from the same or from different materials as the conductors 170, 180.

The material or materials used to form the conductors 170, 180 and the surface conductor layers 270, 280 may include any electrical conductor. Preferable electrical conductors are non-ionizing, such that the material does not undergo a net oxidation or a net reduction during analysis of the sample. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. If a surface conductor layer is not present on a conductor, the conductor is preferably made from a non-ionizing material.

The surface conductor material may be disposed on the conductors 170, 180 by any conventional means compatible with the operation of the test sensor, including foil deposition, chemical vapor deposition, slurry deposition, and the like. In the case of slurry deposition, the mixture may be applied as an ink to the conductors 170, 180, as described in U.S. Pat. No. 5,798,031, for example.

The reagent compositions 275 and 285 may be disposed on or near the conductors 170 and 180, respectively. The term "on" is defined as "above" and is relative to the orientation being described. For example, if a first element is deposited over at least a portion of a second element, the first element is said to be "on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating may be described as "on" the first element. Thus, the use of the term "on" may or may not mean that the two elements being related are in physical contact.

The reagent compositions include reagents and a binder. The binder includes at least one polymeric material that is substantially water-soluble, and optionally may include substantially water-insoluble porous particles. The porous particles may provide additional physical structure to the polymeric material. The binder may form a gel or gel-like material when hydrated by the sample. An optional layer 290 may be disposed on the conductor 170 and/or the surface conductor 270. The optional layer 290 may lack one or more constituents of the reagent composition 275.

The reagent compositions 275 and 285 may include the same or different reagents. When including the same reagents, the reagent compositions 275 and 285 may be the same composition. When including different reagents, the reagents present in the first composition 275 may be selected for use with the working electrode 175, while the reagents present in the second composition 285 may be selected for use with the counter electrode 185. For example, the reagents in the composition 285 may include a mediator to facilitate the free flow of electrons between the sample and the conductor 180. Similarly, the reagents in the composition 275 may include an enzyme system and optionally a mediator to facilitate the reaction of the analyte.

The enzyme system included in the reagent composition 275 may be specific to the analyte and may facilitate the reaction of the analyte while enhancing the specificity of the sensor system to the analyte, especially in complex biological samples. The enzyme system may include one or more enzyme, cofactor, and/or other moiety that participates in a redox reaction with the analyte. For example, an alcohol oxidase can be used to provide a test sensor that is sensitive to the presence of alcohol in a sample. Such a system could be useful in measuring blood alcohol concentrations. In another example, glucose dehydrogenase or glucose oxidase may be used to provide a test sensor that is sensitive to the presence of glucose in a sample. This system could be useful in measuring blood glucose concentrations, for example in patients known or suspected to have diabetes.

The reagent compositions 275, 285 may be disposed by any convenient means, such as printing, liquid deposition, or ink-jet deposition. For example, one or more reagent fluids may be deposited on the test sensor, and the reagent fluid(s) may be dried to form the reagent compositions 275, 285. Examples of devices and methods for depositing a reagent fluid on an electrode of a test sensor are disclosed, for example, in U.S. Patent Pub. US 2009/0145756 A1, with applicant Boru Zhu et al.

A variety of factors may affect the resulting dimensions of the reagent compositions 275, 285. Examples of such factors include the viscosity of a reagent fluid being applied, the screen-size and emulsion combination, and the dimensions of the features of the sensor on which the reagent fluid is deposited. When thinner reagent compositions are preferred, methods other than printing, such as micro-pipetting, ink jetting or pin-deposition, may be used. These methods typically give the dry reagent compositions a micrometer or sub-micrometer thickness, such as 1-10 μm. For example, pin-deposition methods may provide average reagent composition thicknesses of 1 μm. The thickness of the reagent composition resulting from pin-deposition, for example, may be controlled by the amount of binder included in the reagent composition, with higher binder content providing thicker reagent compositions.

The ingredients of a reagent composition, such as 275, 285, may be quantified relative to the dimensions of the composition, or the ingredients may be quantified relative to another dimension of a sensor on which the composition is disposed, such as the reservoir volume or the working electrode area. In one example, an ingredient of a reagent composition may be quantified in terms of micrograms (μg), nanograms (ng), nanomoles (nmol), or enzyme units (U) per square millimeter (mm$^2$) of the reagent composition surface area, where the reagent composition surface area is the 2-dimensional area of the reagent composition. In another example, an ingredient of a reagent composition may be quantified in terms of micrograms (μg), nanomoles (nmol), or enzyme units (U) per microliter (μL) of the reservoir volume. In another example, an ingredient of a reagent composition may be quantified in terms of micrograms (μg), nanomoles (nmol), or enzyme units (U) per square millimeter (mm$^2$) of the working electrode area.

A reagent composition preferably includes a binder. Suitable substantially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), ethyl hydroxyethyl cellulose, carboxymethyl ethyl cellulose, polyvinyl pyrrolidone (PVP), polyamino acids such as polylysine, polystyrene sulfonate, gelatin, acrylic acid, methacrylic acid, maleic anhydride salts thereof, derivatives thereof, and combinations thereof. Polymeric materials include monomers, pre-polymers, and other materials that form or have repeating units. Other polymeric materials may be used.

Among these polymeric materials, PEO, PVA, CMC, and HEC are preferred, with HEC being more preferred at present. For HEC, weight average molecular weights ($M_w$) from about 8,000 to about 1,000,000 are preferred, with $M_w$ from about 15,000 to about 500,000 being more preferred, and $M_w$ from about 90,000 to about 300,000 being more preferred. At present, a mixture of HEC having $M_w$ of about 90,000 and of HEC having $M_w$ of about 300,000 is especially preferred.

The reagent composition preferably includes from about 0.14 to about 0.43 μg of a binder per mm$^2$ of the reagent composition surface area, more preferably includes from about 0.17 to about 0.38 μg/mm$^2$ of a binder, and more preferably includes from about 0.22 to about 0.35 μg/mm$^2$ of a binder. The reagent composition preferably includes from about 1 to about 3 μg of a binder per μL of the reservoir volume, more preferably includes from about 1.2 to about 2.6 μg/μL of a binder, and more preferably includes from about 1.5 to about 2.3 μg/μL of a binder. The reagent composition preferably includes from about 1 to about 7.5 μg of a binder per mm$^2$ of the working electrode area, more preferably includes from about 1.2 to about 6.5 μg/mm$^2$ of a binder, and more preferably includes from about 1.5 to about 5.7 μg/mm$^2$ of a binder.

The reagent composition optionally includes substantially water-insoluble porous particles. Preferably, if the porous particles are present in the reagent composition, a ratio of about 1:10 (w/w) is maintained between the porous particles and the binder. Other ratios may be used to provide different properties to the reagent composition. Examples of porous particles for reagent compositions are disclosed, for example, in U.S. Patent Pub. 2009/0178936 A1, with applicant Boru Zhu.

The reagent composition preferably includes a buffer salt. When the reagent composition is brought into contact with an aqueous sample, the buffer salt preferably maintains the pH of the mixture from about 4.5 to about 7.5, more preferably from about 6 to about 7. The preferred pH and buffer salt(s) for the reagent composition may be chosen to maintain the activity of the enzyme. Phosphate based buffers are presently preferred, but others may be used. Preferably the buffer salt includes $Na_2HPO_4$.

The reagent composition preferably includes from about 2.30 to about 9.54 nmol of a buffer salt per mm$^2$ of the reagent composition surface area, more preferably includes from about 2.80 to about 6.43 nmol/mm$^2$ of a buffer salt, and more preferably includes from about 3.40 to about 4.77 nmol/mm$^2$ of a buffer salt. The reagent composition preferably includes from about 16 to about 67 nmol of a buffer salt per μL of the reservoir volume, more preferably includes from about 20 to about 45 nmol/μL of a buffer salt, and more preferably includes from about 24 to about 34 nmol/μL of a buffer salt. The reagent composition preferably includes from about 16 to about 167 nmol of a buffer salt per mm$^2$ of the working electrode area, more preferably includes from about 20 to about 113 nmol/mm$^2$ of a buffer salt, and more preferably includes from about 24 to about 84 nmol/mm$^2$ of a buffer salt.

The reagent composition may include a one or two electron substantially water-soluble mediator. Mediators may be separated into two groups based on their electrochemical activity. One electron transfer mediators are chemical moieties capable of taking on one additional electron during the conditions of the electrochemical reaction, while two electron transfer mediators are chemical moieties capable of taking on two additional electrons during the conditions of the reaction. Examples of one electron transfer mediators include compounds, such as 1,1'-dimethyl ferrocene, ferrocyanide and ferricyanide, and ruthenium(III) and ruthenium(II) hexaamine.

While other mediators may be used, two electron transfer mediators may be preferred for their ability to transfer approximately twice as many electrons from the enzyme system to the working electrode for the same molar amount of mediator in relation to one electron transfer mediators. Thus, in comparison to one electron transfer mediators, smaller amounts of two electron transfer mediators may be used in the reagent composition. For example, the amount of a two electron transfer mediator may be half of the amount of a one electron transfer mediator.

Examples of two electron transfer mediators include the organic quinones and hydroquinones, such as phenathroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Preferred two electron transfer mediators include 3-phenylimino-3H-phenothiazines (PIPT) and 3-phenylimino-3H-phenoxazines (PIPO). More preferred two electron transfer mediators include the carboxylic acid or salt, such as ammonium salts, of phenothiazine derivatives. At present, especially preferred two electron transfer mediators include (E)-2-(3H-phenothiazine-3-ylideneamino)benzene-1,4-disulfonic acid, (E)-5-(3H-phenothiazine-3-ylideneamino) isophthalic acid, ammonium (E)-3-(3H-phenothiazine-3-ylideneamino)-5-carboxybenzoate, and combinations thereof. Examples of additional two electron transfer mediators include the electro-active organic molecules described in U.S. Pat. Nos. 5,393,615; 5,498,542; and 5,520,786.

The two electron transfer mediators listed above may include inorganic, non-transition metal salt as an impurity. The inorganic, non-transition metal salt typically is an alkali metal or alkaline earth metal salt of the sulfate ion, $[SO_4]^{2-}$.

For example, (E)-2-(3H-phenothiazine-3-ylideneamino)benzene-1,4-disulfonic acid may include inorganic, non-transition metal salt as an impurity, with a mass percentage relative to the mediator from 1% (w/w) to 50% (w/w), such as from 3% (w/w) to 30% (w/w), from 4% (w/w) to 25% (w/w), and from 5% (w/w) to 21% (w/w).

The reagent composition preferably includes from about 1.70 to about 4.76 nmol of a mediator per mm$^2$ of the reagent composition surface area, more preferably includes from about 2.30 to about 5.14 nmol/mm$^2$ of a mediator, and more preferably includes from about 2.80 to about 4.00 nmol/mm$^2$ of a mediator. The reagent composition preferably includes from about 12 to about 40 nmol of a mediator per μL of the reservoir volume, more preferably includes from about 16 to about 36 nmol/μL of a mediator, and more preferably includes from about 20 to about 28 nmol/μL of a mediator. The reagent composition preferably includes from about 12 to about 100 nmol of a mediator per mm$^2$ of the working electrode area, more preferably includes from about 16 to about 90 nmol/mm$^2$ of a mediator, and more preferably includes from about 20 to about 70 nmol/mm$^2$ of a mediator. The reagent composition preferably includes at most 4.76 nmol of a mediator per mm$^2$ of the reagent composition surface area, at most 40 nmol of a mediator per μL of the reservoir volume, or at most 100 nmol of a mediator per mm$^2$ of the working electrode area.

The reagent composition also includes a substantially water-soluble enzyme system. Preferable enzymes for use in the enzyme system of the reagent composition include alcohol dehydrogenase, lactate dehydrogenase, β-hydroxybutyrate dehydrogenase, glucose-6-phosphate dehydrogenase, glucose dehydrogenase, formaldehyde dehydrogenase, malate dehydrogenase, and 3-hydroxysteroid dehydrogenase. Preferable enzyme systems are oxygen independent, thus not substantially oxidized by oxygen.

One such oxygen independent enzyme family is glucose dehydrogenase (GDH). Using different co-enzymes or co-factors, GDH may be mediated in a different manner by different mediators. Depending on their association with GDH, a co-factor, such as flavin adenine dinucleotide (FAD), can be tightly held by the host enzyme, such as in the case of FAD-GDH; or a co-factor, such as Pyrroloquinolinequinone (PQQ), may be covalently linked to the host enzyme, such as with PQQ-GDH. The co-factor in each of these enzyme systems may either be permanently held by the host enzyme or the co-enzyme and the apo-enzyme may be reconstituted before the enzyme system is added to the reagent fluid. The co-enzyme also may be independently added to the host enzyme moiety in the reagent fluid to assist in the catalytic function of the host enzyme, such as in the cases of nicotinamide adenine dinucleotide NAD/NADH$^+$ or nicotinamide adenine dinucleotide phosphate NADP/NADPH$^+$.

The reagent composition preferably includes from about 0.07 to about 0.3 active unit (U, as specified by the manufacturer) of an enzyme system per mm$^2$ of the reagent composition surface area, more preferably includes from about 0.09 to about 0.25 U/mm$^2$ of an enzyme system, and more preferably includes from about 0.1 to about 0.2 U/mm$^2$ of an enzyme system. The reagent composition preferably includes from about 0.5 to about 1.8 U of an enzyme system per μL of the reservoir volume, more preferably includes from about 0.6 to about 1.6 U/μL of an enzyme system, and more preferably includes from about 0.8 to about 1.4 U/μL of an enzyme system. The reagent composition preferably includes from about 0.5 to about 5 U of an enzyme system per mm$^2$ of the working electrode area, more preferably includes from about 0.6 to about 4 U/mm$^2$ of an enzyme system, and more preferably includes from about 0.8 to about 3.5 U/mm$^2$ of an enzyme system.

The reagent composition preferably includes a non-ionic surfactant. The surfactant can be any non-ionic surfactant that assists in the formation of a colloidal suspension of the desired viscosity and stability and that is compatible with the deposition method and analysis. Examples of non-ionic surfactants include saccharide-based surfactants, such as N-heptanoyl-N-methylglucamine, N-octanoyl-N-methyl-glucamine, N-nonanoyl-N-methylglucamine, N-decanoyl-N-methylglucamine, octyl β-D-glucopyranoside, hexyl β-D-glucopyranoside, and n-heptyl β-D-glucopyranoside. At present, saccharide-based surfactants such as N-octanoyl-N-methyl-D-glucamine (sold as MEGA 8 and available from DOJINDO, Gaithersburg, Md.) are preferred. This surfactant includes approximately eight oxyethylene units per molecule, for example. Other preferred surfactants are the ethoxylate based neutral surfactants, such as the PEG-30 tetramethyl decynediol surfactants (SURFYNOL 485, for example, as available from Air Products, Allentown, Pa.). Surfactants that increase the sample fill rate of the sensor and/or assist in stabilizing the enzyme system are preferred.

The reagent composition preferably includes from about 0.04 to about 0.24 μg of a non-ionic surfactant per mm$^2$ of the reagent composition surface area, more preferably includes from about 0.07 to about 0.21 μg/mm$^2$ of a non-ionic surfactant, and more preferably includes from about 0.09 to about 0.18 μg/mm$^2$ of a non-ionic surfactant. The reagent composition preferably includes from about 0.3 to about 1.7 μg of a non-ionic surfactant per μL of the reservoir volume, more preferably includes from about 0.5 to about 1.5 μg/μL of a non-ionic surfactant, and more preferably includes from about 0.6 to about 1.3 μg/μL of a non-ionic surfactant. The reagent composition preferably includes from about 0.3 to about 4.3 μg of a non-ionic surfactant per mm$^2$ of the working electrode area, more preferably includes from about 0.5 to about 3.8 μg/mm$^2$ of a non-ionic surfactant, and more preferably includes from about 0.6 to about 3.2 μg/mm$^2$ of a non-ionic surfactant.

The reagent composition optionally includes an anionic surfactant. The surfactant can be any anionic surfactant that assists in the formation of a well defined perimeter of the reagent composition and that is compatible with the deposition method and analysis. Examples of anionic surfactants include phosphate esters, such as alkylphenol ethoxylate phosphates; sulfates, such as alkylphenol ethoxylate sulfates; and sulfonates, such as alkyl and heteroalkyl sulfonates. Specific examples of anionic surfactants include the nonylphenol ethoxylate phosphates Phospholan CS131 and Phospholan CS141, sodium nonylphenol ethoxylate sulfate (Witcolate D-51-53), sodium methyl cocoyl taurate (Geropon TC-42) and sodium dioctyl sulfosuccinate.

The reagent composition preferably includes from about 3 to 16 nanograms (ng) of an anionic surfactant per mm$^2$ of the reagent composition surface area, more preferably includes from 4 to 12 ng/mm$^2$ of an anionic surfactant, and more preferably includes from 5.5 to 9 ng/mm² of an anionic surfactant. The reagent composition preferably includes from about 20 to 140 ng of an anionic surfactant per µL of the reservoir volume, more preferably includes from 30 to 80 ng/µL of an anionic surfactant, and more preferably includes from 35 to 60 ng/µL of an anionic surfactant. The reagent composition preferably includes from about 10 to 350 ng of an anionic surfactant per mm² of the working electrode area, more preferably includes from 30 to 220 ng/mm² of an anionic surfactant, and more preferably includes from 40 to 150 ng/mm² of an anionic surfactant.

The reagent composition preferably is a low total salt reagent composition, which has a lower concentration of buffer salt and/or a lower concentration of other salts than a conventional reagent composition. Preferably the low total salt reagent composition includes at most 9.54 nmol of a buffer salt per mm² of the reagent composition surface area, and at most 20% (w/w) inorganic, non-transition metal salt in the mediator. More preferably the low total salt reagent composition includes at most 6.43 nmol of a buffer salt per mm² of the reagent composition surface area, and at most 10% (w/w) inorganic, non-transition metal salt in the mediator. More preferably the low total salt reagent composition includes at most 4.77 nmol of a buffer salt per mm² of the reagent composition surface area, and at most 5% (w/w) inorganic, non-transition metal salt in the mediator.

Preferably the low total salt reagent composition includes at most 67 nmol of a buffer salt per µL of the reservoir volume, and at most 20% (w/w) inorganic, non-transition metal salt in the mediator. More preferably the low total salt reagent composition includes at most 45 nmol of a buffer salt per µL of the reservoir volume, and at most 10% (w/w) inorganic, non-transition metal salt in the mediator. More preferably the low total salt reagent composition includes at most 34 nmol of a buffer salt per µL of the reservoir volume, and at most 5% (w/w) inorganic, non-transition metal salt in the mediator.

Preferably the low total salt reagent composition includes at most 167 nmol of a buffer salt per mm² of the working electrode area, and at most 20% (w/w) inorganic, non-transition metal salt in the mediator. More preferably the low total salt reagent composition includes at most 113 nmol of a buffer salt per mm² of the working electrode area, and at most 10% (w/w) inorganic, non-transition metal salt in the mediator. More preferably the low total salt reagent composition includes at most 84 nmol of a buffer salt per mm² of the working electrode area, and at most 5% (w/w) inorganic, non-transition metal salt in the mediator.

Examples of reagent compositions are listed in Table 1, below. These compositions were disposed on the working and counter electrodes of test sensors, where the working electrode had an average diameter from about 0.2 mm² to about 0.5 mm², and the ratio of the counter electrode diameter to the working electrode diameter was at least 1.2. The reservoir volume of the test sensors was about 0.5 µL. The average diameter of each of the reagent compositions was about 2.1 mm, providing an average reagent composition surface area of about 3.5 mm².

TABLE 1

Reagent Compositions

|  | A | B | C | D | E |
| --- | --- | --- | --- | --- | --- |
| Mediator [1] | 14 nmol * | 14 nmol * | 14 nmol ** | 14 nmol ** | 14 nmol ** |
| FAD-GDH enzyme | 0.67 U | 0.67 U | 0.67 U | 0.67 U | 0.67 U |
| HEC (300k) binder | 0.83 µg | 0.83 µg | 0.83 µg | 0.83 µg | 0.83 µg |
| $Na_2HPO_4$ buffer salt | 33.4 nmol | 16.7 nmol | 33.4 nmol | 25.1 nmol | 16.7 nmol |
| MEGA-8 surfactant | 0.64 µg | 0.64 µg | 0.64 µg | 0.64 µg | 0.64 µg |

[1] (E)-2-(3H-phenothiazine-3-ylideneamino)benzene-1,4-disulfonic acid
* Includes 5% (w/w) inorganic, non-transition metal salt
** Includes 20.6% (w/w) inorganic, non-transition metal salt Reagent compositions A and B listed in Table 1 were low total salt reagent compositions. Compositions A and B included at most 9.64 nmol of buffer salt per mm² of the reagent composition surface area, and the mediator in these compositions included less than 20% (w/w) inorganic, non-transition metal salt. In contrast, reagent compositions C, D and E listed in Table 1 were not low total salt reagent compositions. Although compositions C, D and E included at most 9.64 nmol of buffer salt per mm² of the reagent composition surface area, the mediator in these compositions included more than 20% (w/w) inorganic, non-transition metal salt.

Examples of low total salt reagent compositions are listed in Table 2, below. These compositions were disposed on the working and counter electrodes of test sensors, where the working electrode had an average diameter from about 0.2 mm² to about 0.5 mm², and the ratio of the counter electrode diameter to the working electrode diameter was at least 1.2. The reservoir volume of the test sensors was about 0.5 µL. The average diameter of each of the reagent compositions F and G was about 2.3 mm, providing an average reagent composition surface area of about 4.2 mm². The average diameter of each of the reagent compositions H-K was about 2.1 mm, providing an average reagent composition surface area of about 3.5 mm².

TABLE 2

Low Total Salt Reagent Compositions

|  | F | G | H | J | K |
|---|---|---|---|---|---|
| Mediator[1] | 20 nmol | 20 nmol | 18 nmol | 18 nmol | 16 nmol |
| FAD-GDH enzyme | 0.85 U | 0.85 U | 0.4 U | 0.4 U | 0.4 U |
| HEC (300k) binder | 1.28 μg | 1.28 μg | 0.4 μg | 0.4 μg | 0.4 μg |
| HEC (90k) binder | — | — | 0.726 μg | 0.726 μg | 0.726 μg |
| $Na_2HPO_4$ buffer salt | 25.5 nmol | 25.5 nmol | 22.5 nmol | 22.5 nmol | 22.5 nmol |
| MEGA-8 surfactant | 0.5 μg | 0.5 μg | 0.45 μg | 0.45 μg | 0.45 μg |
| Ionic surfactant | — | Geropon[2] 0.07 μg | Geropon[2] 0.02 μg | Phospholan[3] 0.043 μg | Geropon[2] 0.02 μg |

[1] (E)-2-(3H-phenothiazine-3-ylideneamino)benzene-1,4-disulfonic acid, including 4% (w/w) inorganic, non-transition metal salt
[2] Geropon TC-42 (sodium methyl cocoyl taurate)
[3] Phospholan CS131 (nonylphenol ethoxylate phosphate)

The reagent compositions listed in Table 1, above, were formed by deposition and drying of reagent fluids having deposited volumes of 0.35 μL. The reagent fluids A'-E' used to form the reagent compositions listed in Table 1 are listed in Table 3, below.

TABLE 3

Reagent Fluids For Reagent Compositions

|  | A' | B' | C' | D' | E' |
|---|---|---|---|---|---|
| Mediator[1] | 40 mM * | 40 mM * | 40 mM ** | 40 mM ** | 40 mM ** |
| FAD-GDH enzyme | 2 U/μL | 2 U/μL | 2 U/μL | 2 U/μL | 2 U/μL |
| HEC (300k) binder (w/w) | 0.25% | 0.25% | 0.25% | 0.25% | 0.25% |
| $Na_2HPO_4$ buffer salt | 100 mM | 50 mM | 100 mM | 75 mM | 50 mM |
| MEGA-8 surfactant (w/w) | 0.2% | 0.2% | 0.2% | 0.2% | 0.2% |

[1] (E)-2-(3H-phenothiazine-3-ylideneamino)benzene-1,4-disulfonic acid
* Includes 5% (w/w) inorganic, non-transition metal salt
** Includes 20.6% (w/w) inorganic, non-transition metal salt The reagent compositions F and G listed in Table 2, above, were formed by deposition and drying of reagent fluids having deposited volumes of 0.34 μL. The reagent compositions H-K listed in Table 2, above, were formed by deposition and drying of reagent fluids having deposited volumes of 0.2 μL. The reagent fluids used to form the reagent compositions listed in Table 1 are listed in Table 4, below.

TABLE 4

Reagent Fluids For Reagent Compositions

|  | F' | G' | H' | J' | K' |
|---|---|---|---|---|---|
| Mediator[1] | 65 mM | 60 mM | 90 mM | 90 mM | 80 mM |
| FAD-GDH enzyme | 2.5 U/μL | 2.5 U/μL | 3.75 U/μL | 3.75 U/μL | 3.75 U/μL |
| HEC (300k) binder (w/w) | 0.375% | 0.375% | 0.2% | 0.2% | 0.2% |
| HEC (90k) binder (w/w) | — | — | 0.362% | 0.362% | 0.362% |
| $Na_2HPO_4$ buffer salt | 75 mM | 75 mM | 112.5 mM | 112.5 mM | 112.5 mM |
| MEGA-8 surfactant (w/w) | 0.15% | 0.15% | 0.225% | 0.225% | 0.225% |

TABLE 4-continued

Reagent Fluids For Reagent Compositions

| | F' | G' | H' | J' | K' |
|---|---|---|---|---|---|
| Ionic surfactant (w/w) | — | Geropon[2] 0.02% | Geropon[2] 0.01% | Phospholan[3] 0.02% | Geropon[2] 0.01% |

[1](E)-2-(3H-phenothiazine-3-ylideneamino)benzene-1,4-disulfonic acid, including 4% (w/w) inorganic, non-transition metal salt
[2]Geropon TC-42 (sodium methyl cocoyl taurate)
[3]Phospholan CS131 (nonylphenol ethoxylate phosphate)

A preferred reagent fluid may be provided by combining a binder, a buffer salt, a mediator, a surfactant, and an enzyme system. Preferred reagent fluids also may be provided that exclude one or both of the mediator and the enzyme system. Water may then be added to form a mixture having the desired stability. The reagent fluid may include fewer or additional ingredients.

The reagent fluid preferably includes from about 0.1 to about 1% (w/w) of a binder, more preferably from about 0.2 to about 0.8% (w/w). At present, an especially preferred reagent fluid includes from about 0.3 to about 0.6% (w/w) of the binder. If optional porous particles are present in the reagent fluid, a ratio of about 1:10 (w/w) is maintained between the porous particle suspension and the polymeric material. Other ratios may be used to provide different viscosities to the reagent fluid. Examples of porous particles for reagent fluids are disclosed, for example, in U.S. Patent Pub. 2009/0178936.

The reagent fluid preferably includes the buffer salt to maintain the pH of the mixture from about 4.5 to about 7.5, more preferably from about 6 to about 7. The preferred pH and buffer or buffers for the reagent fluid may be chosen to maintain the activity of the enzyme. The concentration of buffer salt introduced to the reagent fluid may range from about 30 to about 115 millimolar (mM). Preferably the concentration of buffer salt introduced to the reagent fluid is from about 40 to about 100 mM, more preferably from about 25 to about 75 mM, more preferably from about 30 to about 60 mM, and more preferably is at most 50 mM. Buffer solutions having other concentrations may be used.

The reagent fluid may include a one or two electron transfer substantially water-soluble mediator. The concentration of mediator in the reagent fluid may range from about 25 to about 90 mM. Preferably the concentration of buffer salt introduced to the reagent fluid is from about 30 to about 60 mM, and more preferably from about 35 to about 40 mM. Preferably the amount of inorganic, non-transition metal salt is at most 20% (w/w) in the mediator. More preferably the amount of inorganic, non-transition metal salt is at most 15% (w/w), at most 10% (w/w), at most 5% (w/w) in the mediator, and at most 4% (w/w) in the mediator.

The reagent fluid also may include a substantially water-soluble enzyme system having a unit activity range as specified by the manufacturer from about 1 active unit per microliter (μL) of the reagent fluid to about 4 active units per μL of the reagent fluid, more preferably from about 1.5 active unit per μL of the reagent fluid to about 2 active units per μL of the reagent fluid. As the solid weight of the enzyme required to provide a specific unit activity can vary substantially by formulation batch and manufacturer, the unit activity provided by the manufacturer for a specific weight of the dry enzyme fluid is preferably used to determine the addition amount.

The reagent fluid preferably includes from about 0.05 to about 0.7% (w/w) of a non-ionic surfactant, more preferably from about 0.07 to about 0.5% (w/w). At present, from about 0.1 to about 0.3% (w/w) of a surfactant is especially preferred. The surfactant can be any surfactant that assists in the formation of a colloidal suspension of the desired viscosity and stability and that is compatible with the deposition method and analysis. The reagent fluid optionally includes from about 0.005 to about 0.03% (w/w) of an anionic surfactant, more preferably from about 0.01 to about 0.02% (w/w).

Figure 3:
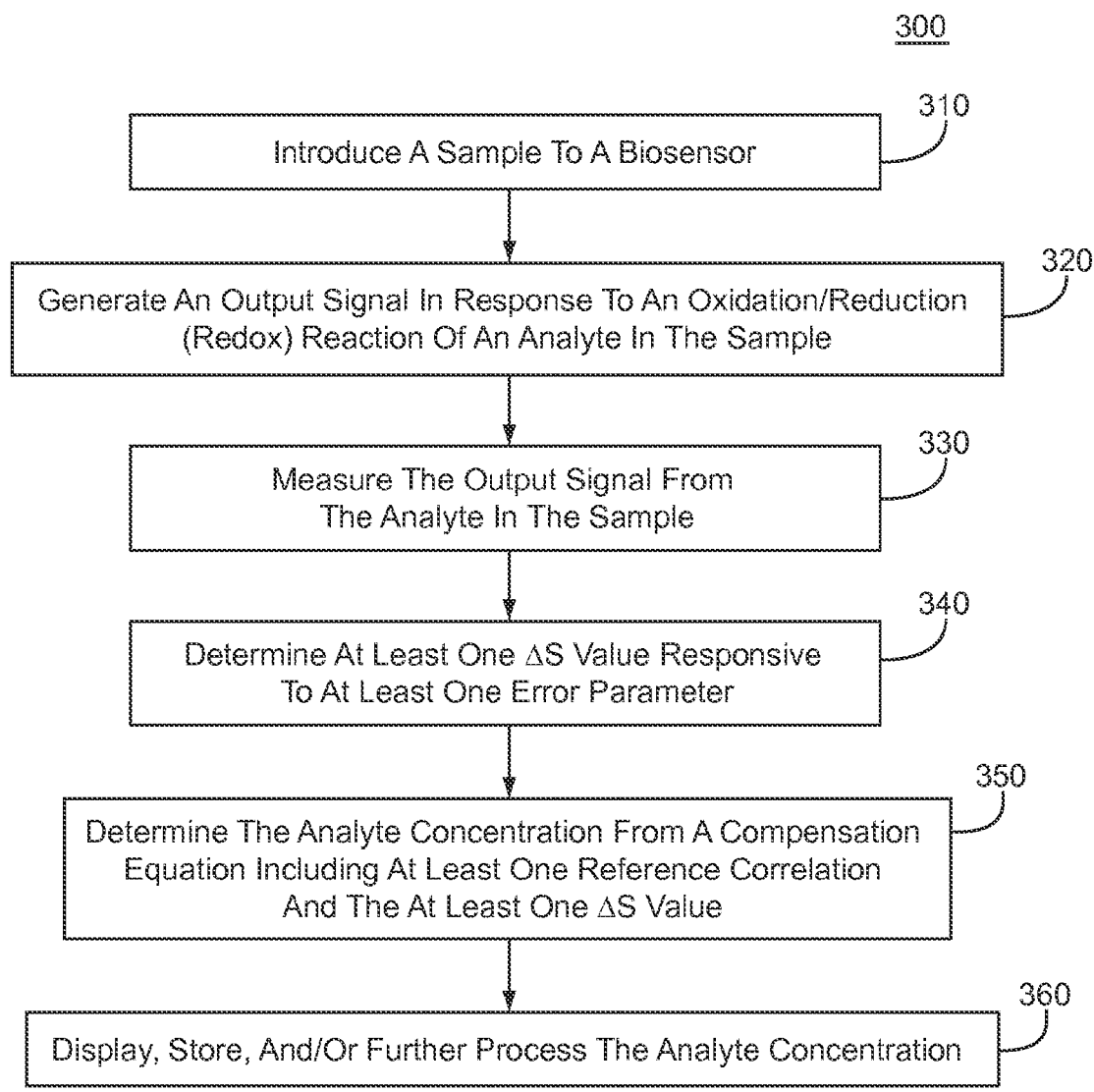
FIG. 3 represents an electrochemical analytic method for determining the presence and/or concentration of an analyte in a sample contacting a low total salt reagent composition.

FIG. 3 represents an electrochemical analytic method 300 for determining the presence and/or concentration of an analyte in a sample contacting a low total salt reagent composition. In 310, the sample is introduced to the biosensor including the low total salt reagent composition. In 320, the biosensor system generates an output signal in response to either a light-identifiable species or an oxidation/reduction (redox) reaction of an analyte in a sample of a biological fluid. In 330, the biosensor system measures the output signal. In 340, at least one ΔS value responsive to at least one error parameter is determined. In 350, the analyte concentration is determined from a compensation equation including at least one reference correlation and at least one ΔS value. In 360, the concentration may be displayed, stored, or the like.

In 310, the sample is introduced to the sensor portion of the biosensor, such as a test sensor. The test sensor includes at least one working and at least one counter electrode. The electrodes may include one or more reagent compositions, where at least one reagent composition is a low total salt reagent fluid. The same reagent composition may be used on the working and counter electrodes, or different reagent compositions may be used to facilitate the operation of the electrodes. For example, the reagent composition at the working electrode may facilitate the reaction of the analyte, e.g. enzyme system and mediator, while the reagent composition at the counter electrode may facilitate the free flow of electrons between the sample and the surface of the electrode, e.g. a reducible species.

A portion of the analyte present in the sample is chemically or biochemically oxidized or reduced, such as by an oxidoreductase. This occurs as the sample hydrates the reagents in the low total salt reagent composition. Upon oxidation or reduction, electrons optionally may be transferred between the analyte and a mediator. Thus, an ionized measurable species is formed, such as from the analyte or a mediator.

In 320, the biosensor system generates an output signal in response to an oxidation/reduction (redox) reaction of an analyte in a sample of a biological fluid. The output signal may be generated using an electrochemical sensor system. A measurable species, which may be the charged analyte or the charged mediator, is electrochemically excited (oxidized or reduced) with an input signal. Input signals may be electrical signals, such as current or potential, that pulse or turn on and off at a set sequence. The input signal is a sequence of excitation pulses separated by relaxations. During an amperometric pulse, the electrical potential applied during the excitation is preferably applied at a substantially constant voltage and polarity throughout its duration. This directly contrasts to some conventional excitations where the voltage is changed or "swept" through multiple voltage potentials and/or polarities during data recordation.

Input signals may have one or more pulse interval. A pulse interval is the sum of a pulse and the relaxation constituting a duty cycle. Each pulse has an amplitude and a width. The amplitude indicates the intensity of the potential, the current, or the like of the electrical signal. The amplitude may vary or be substantially constant, such as during amperometry, during the pulse. The pulse width is the time duration of the pulse. The pulse widths in an input signal may vary or be substantially the same. Each relaxation has a relaxation width, which is the time duration of the relaxation. The relaxation widths in an input signal may vary or be substantially the same.

By adjusting the width of the excitation and relaxation of the duty cycles, gated input signals may increase the accuracy and/or precision of the analysis. Preferable input signals include at least 2, 3, 4, or 8 duty cycles applied during less than 2, 3, or 5 seconds. More preferably, at least 2 duty cycles are applied within 3 seconds. Preferably, the width of each excitation pulse is independently selected from between 0.1 and 2 seconds and more preferably from between 0.2 and 1 second. At present, especially preferred input signal pulse widths are independently selected from between 0.3 and 0.8 seconds. Preferable pulse intervals are in the range of less than 3, 2.5, or 1.5 seconds. At present, input signals having pulse widths of 0.3 to 0.5 second and pulse intervals from 0.7 to 2 seconds are especially preferred. The input signal may have other pulse widths and intervals.

The biosensor may generate an output signal in response to the measurable species and the input signal. The output signal, such as one or more current values, may be measured continuously or intermittently and may be recorded as a function of time. Suitable output signals may include those that reach a steady-state and those that are transient. Steady-state current values are observed when the current change with respect to time is substantially constant, such as within ±10 or ±5%. Transient current values decay with respect to time.

Preferably, the sample undergoes relaxation. The measurement device may open the circuit through the test sensor, thus allowing relaxation. During the relaxation, the current present during the excitation is substantially reduced by at least one-half, preferably by an order of magnitude, and more preferably to zero. Preferably, a zero current state is provided by an open circuit or other method known to those of ordinary skill in the art to provide a substantially zero current flow. Preferably, the output signal is not recorded during the relaxation.

Preferably, the biosensor continues to apply pulses from the input signal to the working and counter electrodes for the desired time period. The duty cycle including the excitation and the relaxation may be repeated or a duty cycle having different pulse widths and/or intervals may be applied.

In 330, the biosensor system measures the output signal generated by the analyte in response to the input signal applied to the sample, such as from a redox reaction of the analyte. The system may measure the output signal continuously or intermittently. For example, a biosensor system may measure the output signal intermittently during each pulse, resulting in multiple current values during each pulse. The system may show the output signal on a display and/or may store the output signal or portions of the output signal in a memory device.

In 340 of FIG. 3, one or more ΔS values are determined that are responsive to one or more error parameters. ΔS values may be determined for temperature, hematocrit, and other contributors.

In 350, the analyte concentration of the sample is determined from a compensation equation including at least one reference correlation and at least one ΔS value. The biosensor preferably analyzes an output signal current value by correlating one or more current values with the analyte concentration of the sample. Preferably, the output current value that is correlated with the analyte concentration of the sample is recorded from an excitation where the initial current value is greater than those that follow in the decay and within less than about 7 seconds of introducing the sample to the test sensor in 310. More preferably, the output current value that is correlated with the analyte concentration of the sample is obtained within less than about 7 seconds of introducing the sample to the test sensor in 310 and is the first current value recorded from an excitation where the current values that follow the first current value decrease. Even more preferably, the output current value that is correlated with the analyte concentration of the sample is obtained within less than about 7 seconds of introducing the sample to the test sensor in 310, is the first current value recorded from an excitation where the current values that follow the first current value decrease, and is obtained during the maximum kinetic performance of the test sensor. Additional current, time, and/or other values also may be analyzed. In 360, the analyte concentration value may be displayed, stored for future reference, and/or used for additional calculations.

Figure 4:
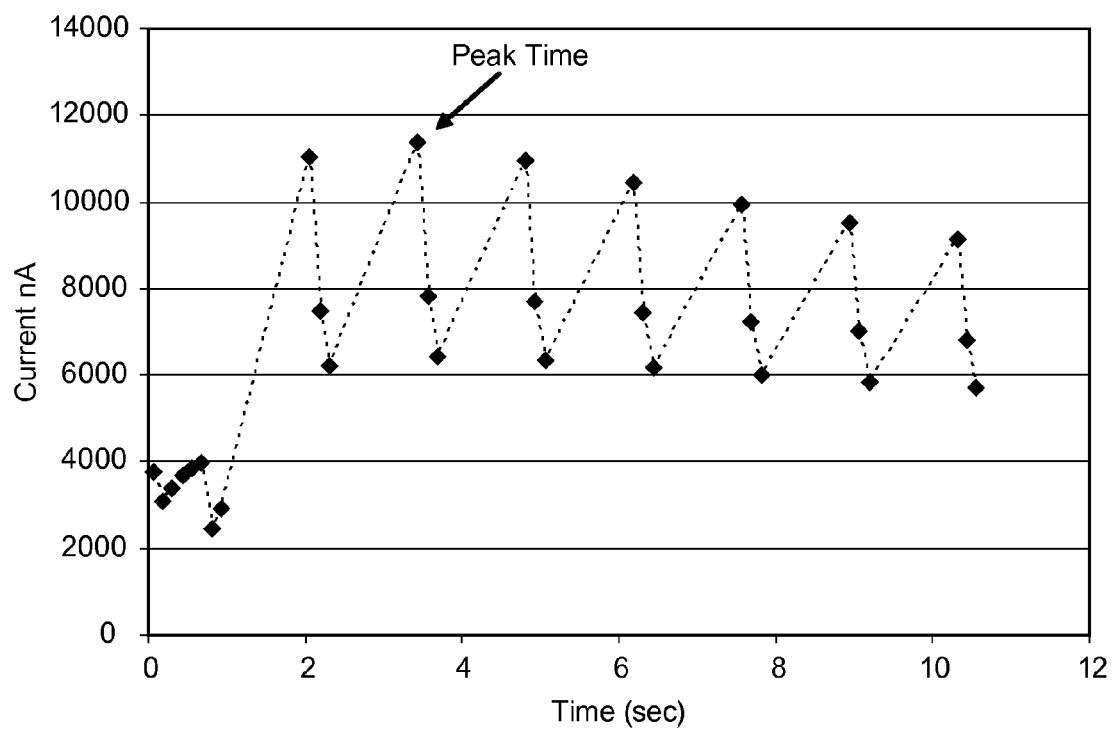
FIG. 4 depicts the output signals from a test sensor for a whole blood sample having a glucose concentration of 400 mg/dL and having a hematocrit content of 70%.

FIG. 4 shows the output signals from a test sensor for a whole blood sample having a glucose concentration of 400 mg/dL and having a hematocrit content of 70%. The signal input to the test sensor by the measurement device was a gated amperometric pulse sequence including eight excitations separated by seven relaxations, such as described in U.S. Patent Pub. 2008/0173552. The second through eighth excitations were about 0.4 second in duration, and the second through seventh relaxations were about 1 second in duration. Three output current values were recorded during the second through eighth excitations.

A correlation of one or more output current values with the analyte concentration of the sample may be prepared by plotting the output current at a particular time in the analysis against a known concentration of the analyte in a series of stock solutions containing the analyte. To correlate the output current values from the input signal with the analyte concentration of the sample, the initial current value from the excitation is preferably greater than those that follow in the decay. Preferably, the output current value or values correlated with the analyte concentration of the sample are taken from a decay including current data reflecting the maximum kinetic performance of the test sensor. The kinetics of the redox reaction underlying the output currents is affected by multiple factors. These factors may include the rate at which the reagent composition rehydrates, the rate at which the enzyme system reacts with the analyte, the rate at which the enzyme system transfers electrons to the mediator, and the rate at which the mediator transfers electrons to the electrode.

The maximum kinetic performance of the test sensor may be reached during an excitation of a gated amperometric pulse sequence when the initial current value of an excitation having decaying current values is greatest for the multiple excitations. Preferably, the maximum kinetic performance of a test sensor is reached when the last in time current value obtained for an excitation having decaying current values is the greatest last in time current value obtained for the multiple excitations. More preferably, the maximum kinetic performance of a test sensor is reached when the initial current value of an excitation having decaying current values is greatest for the multiple excitations and the last in time current value obtained for the same excitation is the greatest last in time current value obtained for the multiple excitations.

The maximum kinetic performance can be described in terms of the parameter "peak time", which is the time at which an electrochemical test sensor obtains its maximum output current value after a sample containing an analyte contacts the test sensor. The maximum output current value is preferably used for correlation with the analyte concentration of the sample. Preferably the peak time for a test sensor is less than about 7 seconds, and more preferably less than about 5 seconds, of introducing the sample to the test sensor. Preferably, the peak time is within about 0.4 to about 7 seconds, more preferably within about 0.6 to about 6.4 seconds, more preferably within about 1 to about 5 seconds, more preferably within about 1.1 to about 3.5 seconds of introducing the sample to the test sensor. In FIG. 4, the maximum kinetic performance is reached at an analysis time of 3.5 seconds, as indicated by the "Peak Time" label identifying the greatest current value for all the recorded excitations.

Figure 5A:
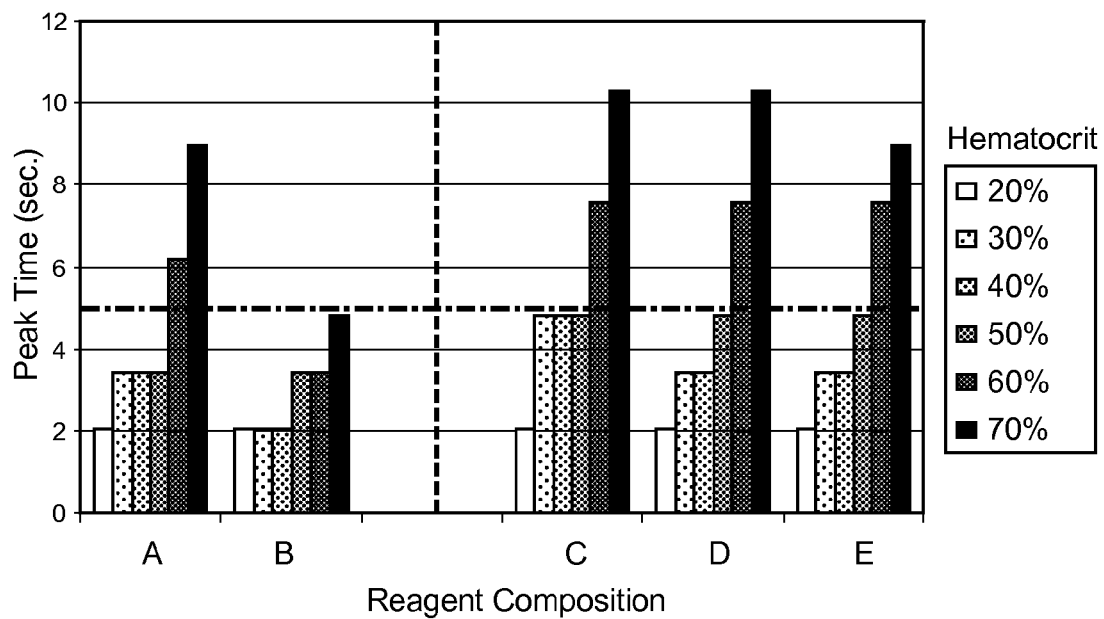
FIG. 5A depicts a graph of peak times for test sensors having the reagent compositions listed in Table 1, in contact with blood samples containing 50 mg/dl glucose and having different levels of hematocrit.
Figure 5B:
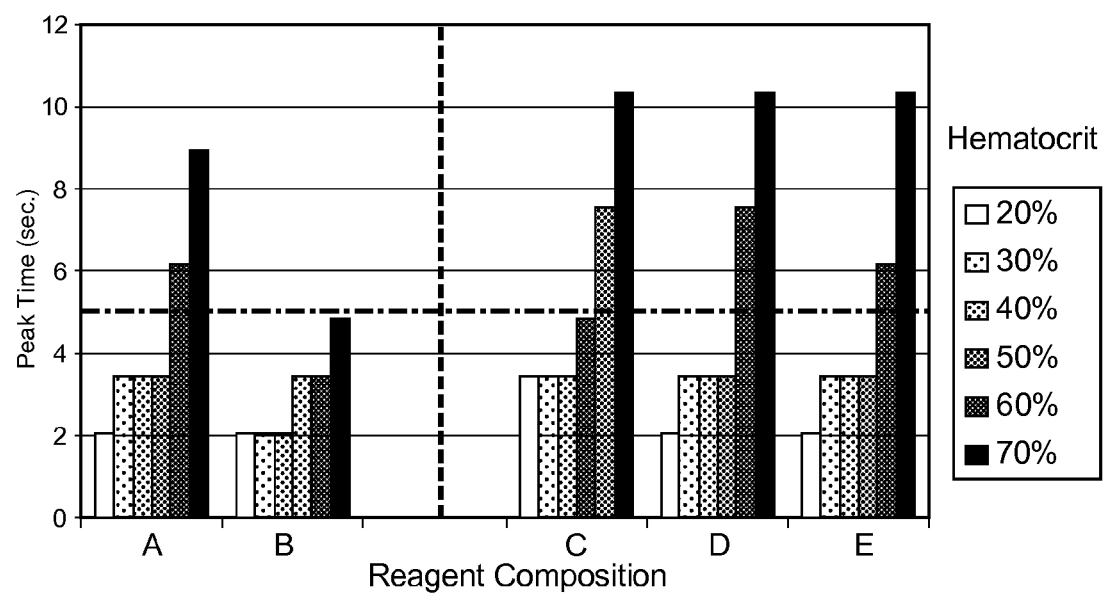
FIG. 5B depicts a graph of peak times for test sensors having the reagent compositions listed in Table 1, in contact with blood samples containing 100 mg/dl glucose and having different levels of hematocrit.
Figure 6A:
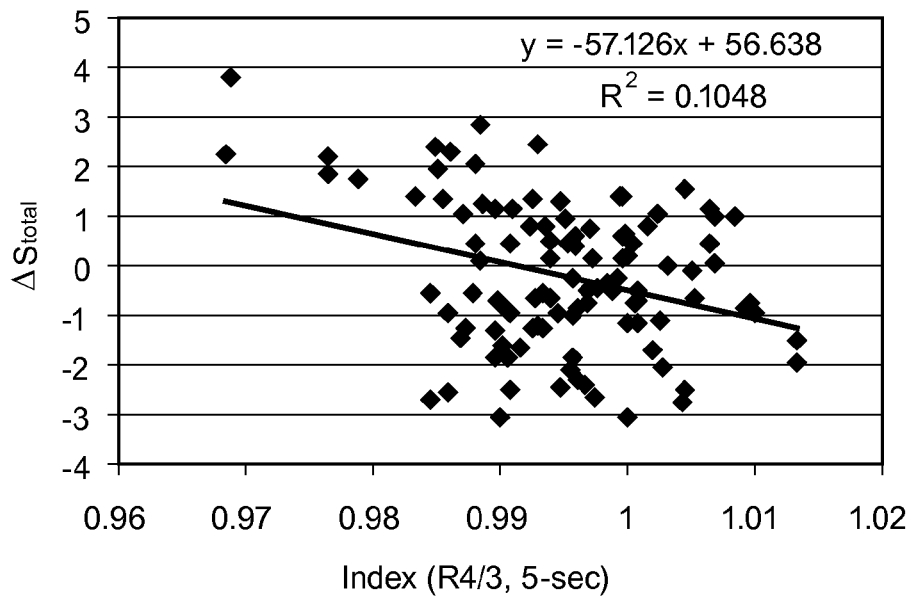
FIG. 6A depicts a graph of the correlations of $\Delta S_{total}$ for samples as a function of a simple ratio index, as measured at 5 seconds after contacting a test sensor having reagent composition A with the sample.
Figure 6B:
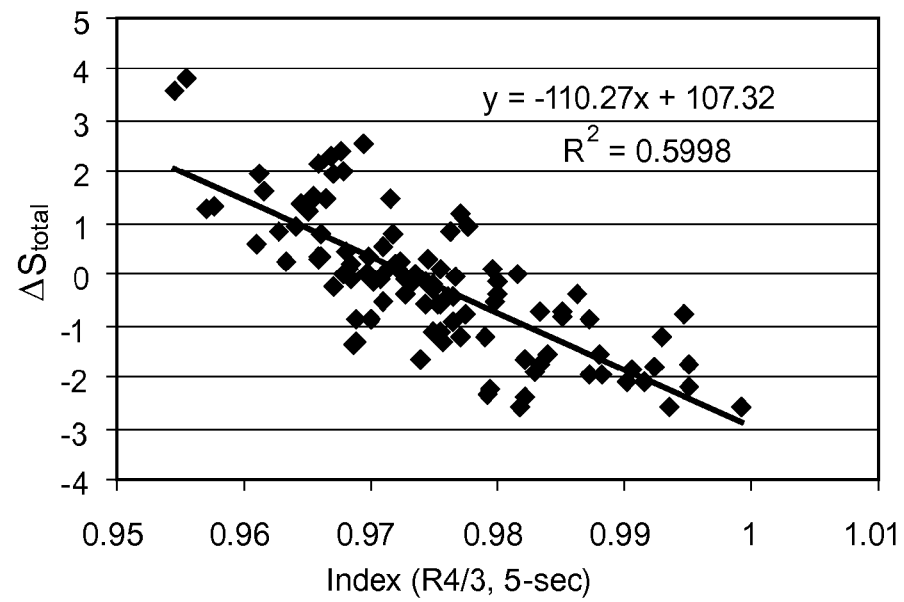
FIG. 6B depicts a graph of the correlations of $\Delta S_{total}$ for samples as a function of a simple ratio index, as measured at 5 seconds after contacting a test sensor having reagent composition B with the sample.
Figure 6C:
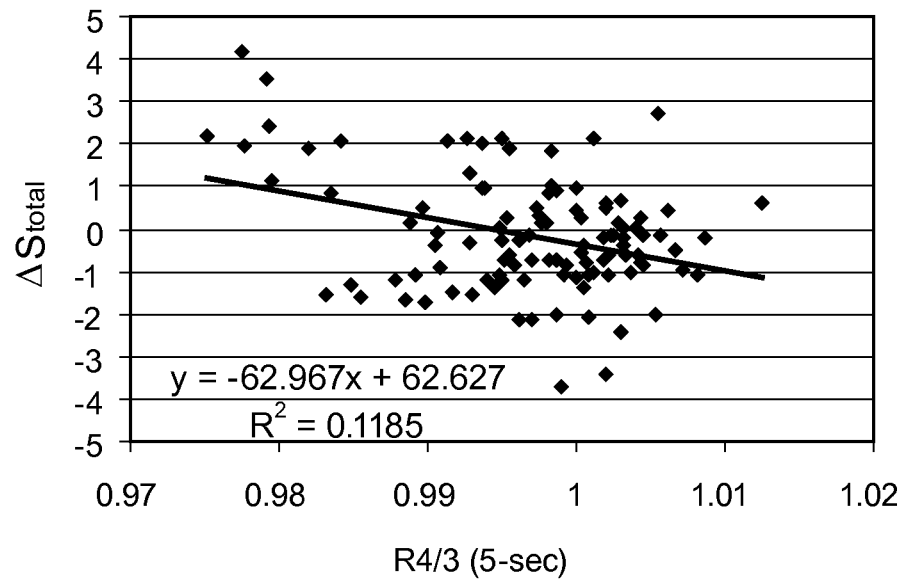
FIG. 6C depicts a graph of the correlations of $\Delta S_{total}$ for samples as a function of a simple ratio index, as measured at 5 seconds after contacting a test sensor having reagent composition C with the sample.
Figure 6D:
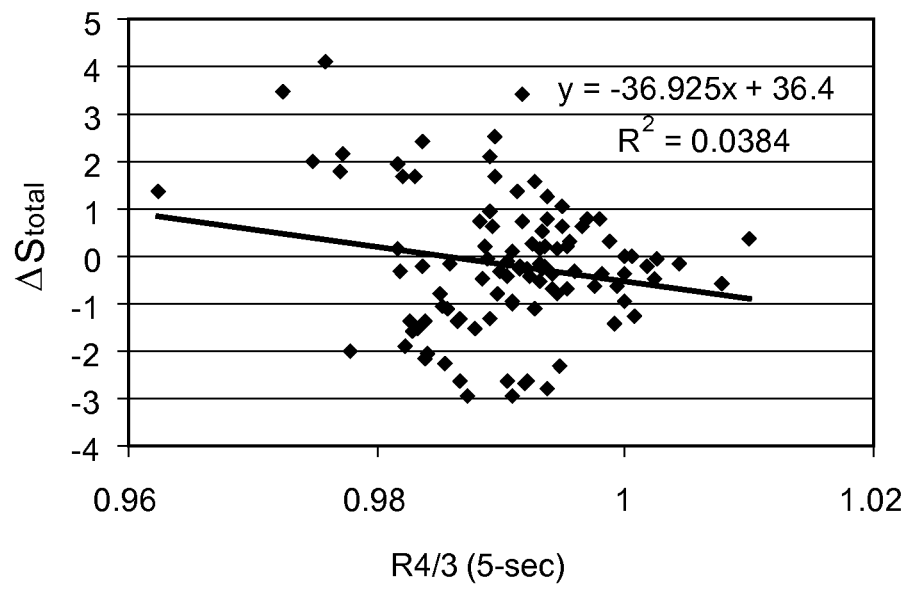
FIG. 6D depicts a graph of the correlations of $\Delta S_{total}$ for samples as a function of a simple ratio index, as measured at 5 seconds after contacting a test sensor having reagent composition D with the sample.
Figure 6E:
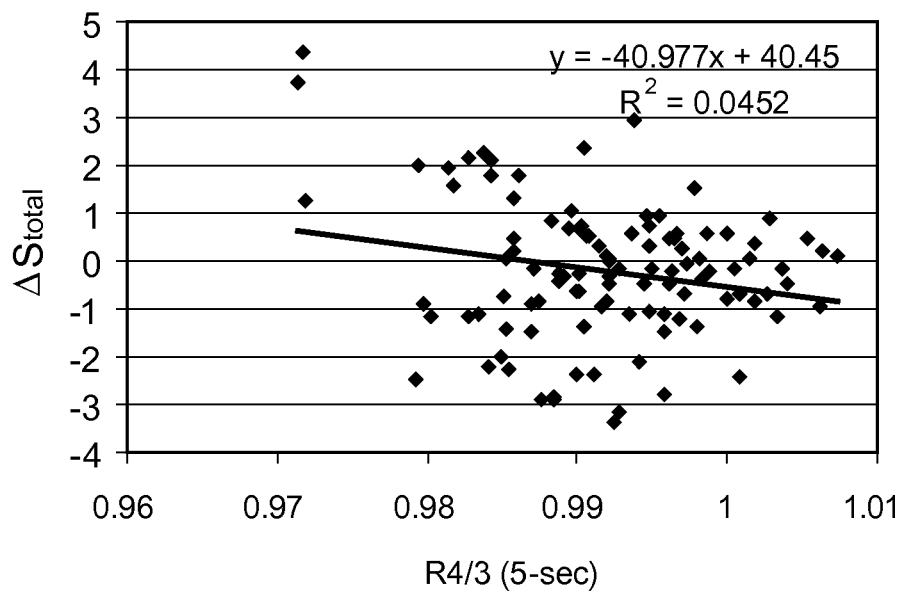
FIG. 6E depicts a graph of the correlations of $\Delta S_{total}$ for samples as a function of a simple ratio index, as measured at 5 seconds after contacting a test sensor having reagent composition E with the sample.

FIGS. 5A and 5B depict graphs of peak times for test sensors having low total salt reagent compositions (A and B) and for test sensors having reagent compositions that were not low total salt compositions (C, D and E). In FIG. 5A, the concentration of glucose in the samples was 50 mg/dl. In FIG. 5B, the concentration of glucose in the samples was 100 mg/dl. The samples had hematocrit contents ranging from 20% to 70%. Each graph plots the peak time as a function of hematocrit content for the reagent compositions A-E listed in Table 1, above. For each composition, the peak times for the hematocrit contents of 20%, 30%, 40%, 50%, 60% and 70% are shown from left to right.

From the results depicted in FIGS. 5A and 5B, a lower content of inorganic, non-transition metal salt in the mediator and a lower buffer salt concentration correlated with shorter peak times. This effect was especially evident for samples having higher hematocrit contents. Thus, a low total salt reagent composition can provide for desirable peak times in the biosensor analysis, even when the sample has a relatively high hematocrit content.

The correlation of one or more output current values with the analyte concentration of the sample may be adjusted to account for errors in the measurement. One approach to correct errors associated with a biosensor analysis is to adjust the correlation for determining analyte concentrations in a sample from output current values with index functions extracted from intermediate current values of the output current values. Index functions can compensate the correlation for determining analyte concentrations from the output current values for one or more errors in the analyses that could result in bias of the determined analyte concentrations. Index functions correspond to the %-bias in the correlation between the analyte concentrations and the output current values due to one or more errors in the analysis.

The %-bias in the correlation may be represented by one or more $\Delta S$ values obtained from one or more error parameters. The $\Delta S$ values represent slope deviations of the correlation between analyte concentrations and output current values determined from one or more error parameters. Index functions corresponding to the slope or change in slope may be normalized to reduce the statistical effect of changes in the output current values, improve the differentiation in variations of the output current values, standardize the measurements of the output current values, a combination thereof, or the like. The adjusted correlation may be used to determine analyte concentrations in biological samples from the output current values and may have improved accuracy and/or precision in comparison to conventional biosensors. Error correction using index functions and $\Delta S$ values is described, for example, in International Patent Application No. PCT/US08/85768, filed Dec. 6, 2008, entitled "Slope-Based Compensation", with inventor Huan-Ping Wu.

Thus, an output current value responsive to sample glucose concentration may be converted into a corrected glucose concentration of the sample using an index function representing $\Delta S/S$. Alternatively, a corrected glucose concentration value may be determined from an uncorrected glucose concentration value using an index function and an equation such as $G_{corr}=G_{raw}/(1+f(Index))$, where $G_{corr}$ is the corrected glucose concentration of the sample, $G_{raw}$ is the determined analyte concentration of the sample without compensation, and f(Index) is an index function.

Index functions may include ratios extracted from an output signal, such as the output signal depicted in FIG. 4. For example, the output signal values may be compared within an individual pulse-signal decay cycle, such as ratio $R3=i_{3,3}/i_{3,1}$, where $i_{3,3}$ denotes the third current value recorded for the third signal decay, and $i_{3,1}$ denotes the first current value recorded for the third signal decay. In another example, the output signal values may be compared between separate pulse-signal decay cycles, such as ratio $R4/3=i_{4,3}/i_{3,3}$, where $i_{3,3}$ denotes the third current value recorded for the fourth signal decay. Index functions may include combinations of ratios extracted from the output signal. In one example, an index function may include a simple ratio of ratios, such as Ratio3/2=R3/R2. In another example, an index function may include a more complicated combination of simpler index functions. For example, an index function Index-1 may be represented as Index-1=R4/3−Ratio3/2. In another example, an index function Index-2 may be represented at Index-2= $(R4/3)^p-(Ratio3/2)^q$, where p and q independently are positive numbers.

Preferably an index function corrects errors associated with variations in hematocrit content. Calculation of such an index function can be facilitated by using a test sensor that produces an output signal that varies with hematocrit content. Surprisingly, a test sensor having a low total salt reagent composition can provide such an output signal.

FIGS. 6A-6E depict graphs of the correlations of $\Delta S_{total}$ as a function of the simple ratio index R4/3. The data for these correlations were taken from glucose output current signals from capillary blood samples at 21.8° C. The reagent compositions of the test sensors of FIG. 6A-FIG. 6E were compositions A-E from Table 1, respectively. The test sensors having low total salt reagent composition B had the best separation of values at the different hematocrit levels.

Table 5 lists the $R^2$ values for the various ratio index functions for the data used to generate the graphs of FIGS. 6A-6E, and for similar data collected at 17.8° C. The $R^2$ values indicate the overall correlation between $\Delta S_{total}$ and the index by the hematocrit content.

TABLE 5

$R^2$ Values For Correlations of $\Delta S_{total}$ and Ratio Index Functions.

| Temperature | Reagent Composition* | R3/2 (3.5 s) | R4/3 (5 s) | R5/4 (6.4 s) | R6/7 (7.8 s) | R7/6 (9.2 s) |
|---|---|---|---|---|---|---|
| 21.8° C. | A | 0.001013 | 0.104764 | 0.565351 | 0.760619 | 0.750959 |
| | B | 0.516962 | 0.599775 | 0.505758 | 0.438291 | 0.31835 |
| | C | 0.091352 | 0.118496 | 0.302064 | 0.408586 | 0.524337 |
| | D | 0.000134 | 0.038426 | 0.218307 | 0.493913 | 0.548401 |
| | E | 0.000457 | 0.045204 | 0.382858 | 0.565626 | 0.637481 |
| 17.8° C. | A | 0.046511 | 0.033404 | 0.201073 | 0.57258 | 0.712873 |
| | B | 0.347457 | 0.561101 | 0.594296 | 0.501804 | 0.529152 |
| | C | 0.145856 | 0.040137 | 0.148183 | 0.363599 | 0.556556 |
| | D | 0.002571 | 0.000171 | 0.089739 | 0.291356 | 0.501046 |
| | E | 0.003322 | 0.018583 | 0.29426 | 0.566881 | 0.588227 |

*Compositions from Table 1.

For output times of 5 seconds or less at 21.8° C., the test sensors having a low total salt reagent composition (composition B) provided correlations having significantly better $R^2$ values than those provided by the other test sensors. For output times of 6.4 seconds or more at 21.8° C., the test sensors having a low total salt reagent composition (composition A) provided correlations having significantly better $R^2$ values than those provided by the other test sensors.

For output times of 6.4 seconds or less at 17.8° C., the test sensors having a low total salt reagent composition (composition B) provided correlations having significantly better $R^2$ values than those provided by the other test sensors. For output times of 7.8 seconds or more at 17.8° C., the test sensors having a low total salt reagent composition (composition A) provided correlations having significantly better $R^2$ values than those provided by the other test sensors. Thus, at lower analysis temperatures, a test sensor having a low total salt reagent composition could provide a better correlation at an earlier assay time than could a test sensor having a reagent composition that was not a low total salt composition.

The index functions from the graphs of FIGS. 6A-6E were used to formulate correlation equations to correct the biosensor analysis bias for samples having different hematocrit contents. Using one or more index functions related to $\Delta S$ may reduce the bias spread, which is defined as the standard deviation of the bias/%-bias population. The correlation between $\Delta S_{total}$ and one or more index functions directly affects the reduction of the standard deviation (SD) of the bias population. Therefore, the higher the $R^2$ value, the larger the reduction of the SD value and, thus, the smaller the bias spread. This experimental relationship is observed in Table 6, where the %-population of the data set within a ±10/±10% bias limit before and after compensation are listed for the reagent compositions listed in Table 1. The %±10% was significantly greater for the test sensors having a low total salt reagent composition, both before and after the compensation equation was applied to the results.

TABLE 6

Accuracy of Correlations of Output With Analyte Concentration.

| | % ± 10% | |
|---|---|---|
| Reagent Composition* | Correlation Before Compensation | Correlation After Compensation |
| A | 78% | 78% |
| B | 86% | 99% |
| C | 81% | 81% |
| D | 81% | 81% |
| E | 80% | 80% |

*Compositions from Table 1.

The improvement provided by a low salt reagent composition is significant, as fewer analyses would be outside of the ±10/±10% accuracy boundary. By reducing the number of analyses outside of the boundary, more of the readings obtained could be used for accurate therapy by a patient. The need to discard and repeat analysis by the patient also may be reduced.

Figure 7:
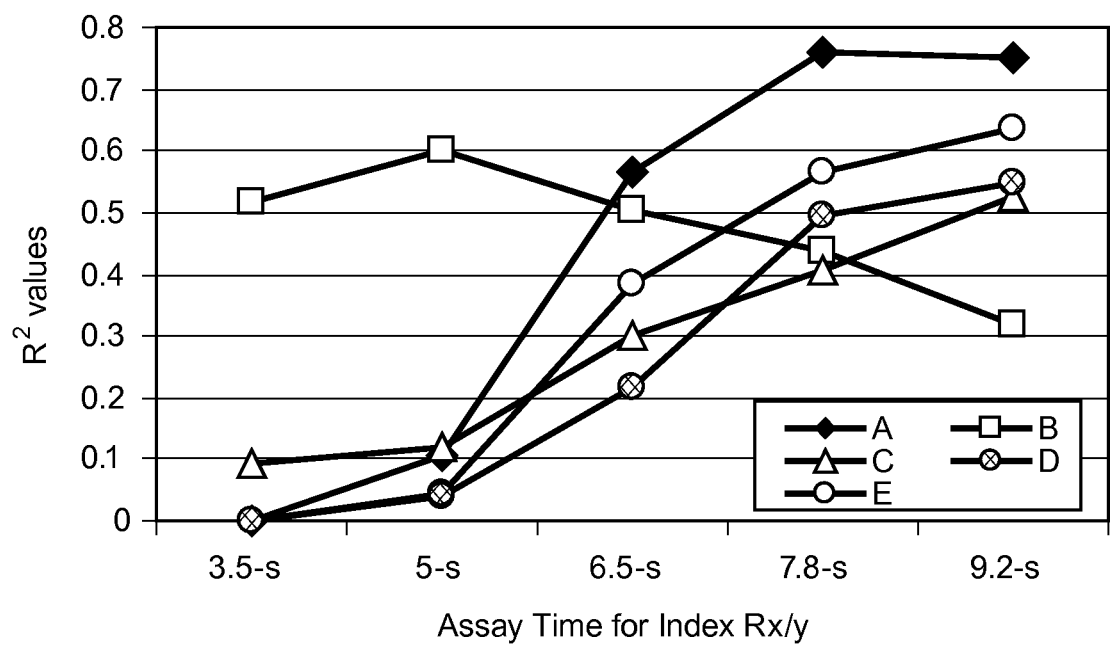
FIG. 7 depicts graphs of the $R^2$ values at 21.8° C. as a function of assay time for test sensors having the reagent compositions listed in Table 1.

FIG. 7 depicts graphs of the $R^2$ values at 21.8° C. as a function of assay time for test sensors having the reagent compositions A-E listed in Table 1. The 3.5 second, 5 second, 6.5 second, 7.8 second and 9.2 second assay times correspond to ratio index functions R3/2, R4/3, R5/4, R6/7 and R7/6, respectively. Thus, FIG. 7 is a graphical depiction of the results listed in the first half of Table 5. For the two earliest assay times (3.5 and 5 seconds), the low total salt reagent composition B provided $R^2$ values of at least 0.5, whereas the other reagent compositions provided $R^2$ values of only 0.12 or less. For an assay time of 6.5 seconds, both the low total salt reagent compositions A and B provided $R^2$ values of at least 0.5, whereas the other reagent compositions provided $R^2$ values of only 0.2-0.4. For assay times longer than 7 seconds, the low total salt reagent composition A provided $R^2$ values of at least 0.5; however, the low total salt reagent composition B provided $R^2$ values below 0.5. For assay times of 7.8 and 9.2 seconds, the $R^2$ values provided by reagent compositions C-E correlated inversely with the buffer salt concentration.

As illustrated by the graphs of FIG. 7, a low total salt reagent composition may provide $R^2$ values of at least 0.5 for index functions corresponding to assay times of at most 6.5 seconds. Thus, a low total salt reagent composition may provide for accurate analysis of an analyte in a sample at shorter assay times than those provided by conventional reagent compositions.

Figure 8:
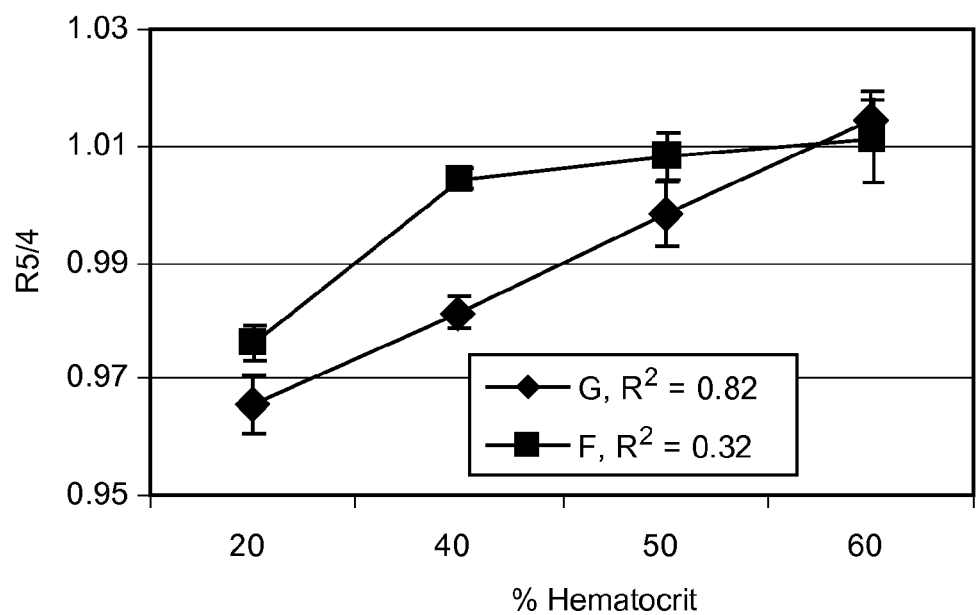
FIG. 8 depicts a graph of the R5/4 indices at 16° C. as a function of hematocrit levels for low total salt reagent compositions F and G.

FIG. 8 depicts a graph of the R5/4 indices at 16° C. as a function of hematocrit levels for low total salt reagent compositions F and G listed in Table 2. These compositions were similar, except that composition G included both a non-ionic surfactant and an anionic surfactant, whereas composition F included a non-ionic surfactant only. The $R^2$ value for the results provided by composition G was 0.82, whereas the $R^2$ value for the results provided by composition F was only 0.32. Thus, the presence of a small amount of an anionic surfactant provided a significant improvement in the R5/4 index function for this system.

Reagent composition B was disposed on the working electrode of a test sensor at various thicknesses. Table 7 lists the concentrations of the mediator on each of four different types of working electrodes. Since the same low salt reagent composition was used for each electrode, a lower concentration correlates with a smaller thickness of the reagent composition on the electrode. Each reagent composition had an enzyme concentration of from 1.21 to 1.50 units per square millimeter ($U/mm^2$). Table 7 also lists the %-population of the data set within a ±10/±10% bias limit for analyses performed at different temperatures. The working electrode with the thinnest layer of low salt reagent composition had the highest percentage of measurements within a ±10/±10% bias limit. This improvement was particularly evident at lower temperatures, such as 11° C.

TABLE 7

Accuracy of Correlations For Low Salt Reagent Layers Having Different Thicknesses.

| Density of Mediator on Working Electrode ($\mu g/mm^2$) | % ± 10% | | |
| --- | --- | --- | --- |
| | 11° C. | 15° C. | 23° C. |
| 1.503 | 94% | 99% | 98% |
| 1.340 | 94% | 96% | 96% |
| 1.290 | 96% | 95% | 100% |
| 1.130 | 99% | 98% | 100% |

Figure 9:
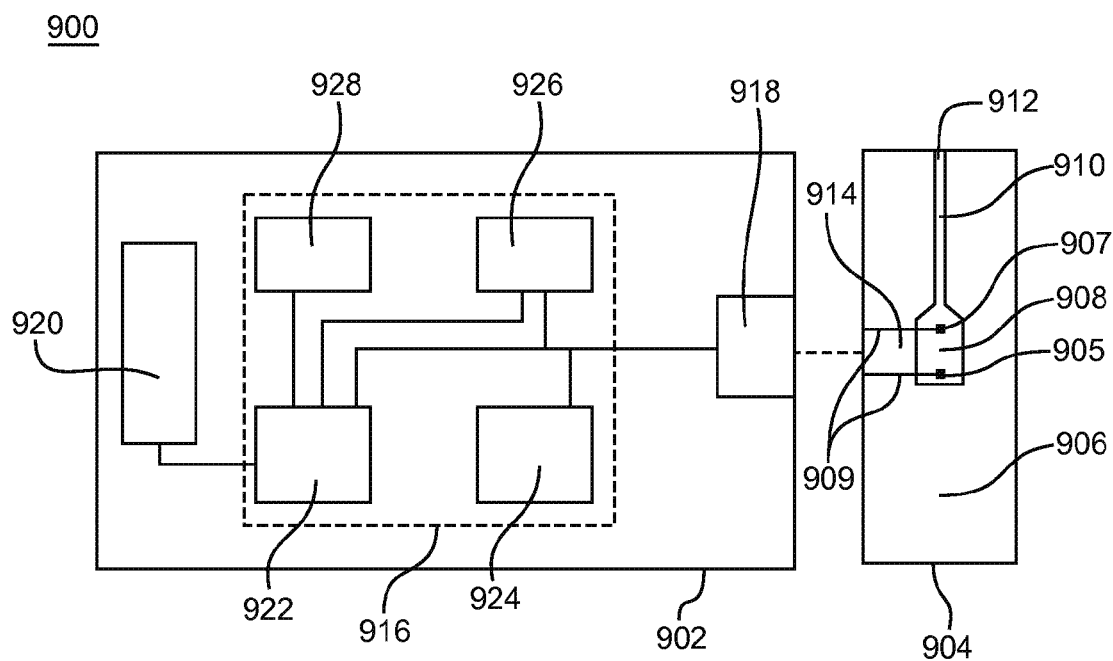
FIG. 9 depicts a schematic representation of a biosensor that determines an analyte concentration in a sample of a biological fluid using a gated amperometric input signal.

FIG. 9 depicts a schematic representation of a biosensor 900 that determines an analyte concentration in a sample of a biological fluid using a gated amperometric input signal. The biosensor 900 includes a measurement device 902 and a test sensor 904, which may be implemented in any analytical instrument, including a bench-top device, a portable or hand-held device, or the like. The biosensor 900 may be utilized to determine analyte concentrations, including those of glucose, uric acid, lactate, cholesterol, bilirubin, and the like. While a particular configuration is shown, the biosensor 900 may have other configurations, including those with additional components.

The test sensor 904 has a base 906 forming a reservoir 908 and a channel 910 with an opening 912. The reservoir 908 and the channel 910 may be covered by a lid with a vent. The reservoir 908 defines a partially-enclosed volume. The reservoir 908 may contain a composition that assists in retaining a liquid sample such as water-swellable polymers or porous polymer matrices. Reagents may be deposited in the reservoir 908 and/or channel 910. The reagent composition at the working electrode 907 includes a low total salt reagent composition and may include one or more enzyme system, mediator, and like species. The counter electrode 905 may be formed using the same or a different reagent composition, preferably one lacking an enzyme system. The test sensor 904 also may have a sample interface 914 disposed adjacent to the reservoir 908. The sample interface 914 may partially or completely surround the reservoir 908. The test sensor 904 may have other configurations.

The sample interface 914 has conductors 909 connected to the working electrode 907 and the counter electrode 905. The electrodes may be substantially in the same plane or in more than one plane. The electrodes 905, 907 may be disposed on a surface of the base 906 that forms the reservoir 908. The electrodes 905, 907 may extend or project into the reservoir 908. A dielectric layer may partially cover the conductors 909 and/or the electrodes 905, 907. The sample interface 914 may have other electrodes and conductors.

The measurement device 902 includes electrical circuitry 916 connected to a sensor interface 918 and a display 920. The electrical circuitry 916 includes a processor 922 connected to a signal generator 924, an optional temperature sensor 926, and a storage medium 928.

The signal generator 924 provides an electrical input signal to the sensor interface 918 in response to the processor 922. The electrical input signal may be transmitted by the sensor interface 918 to the sample interface 914 to apply the electrical input signal to the sample of the biological fluid. The electrical input signal may be a potential or current and may be applied in multiple pulses, sequences, or cycles. The signal generator 924 also may record an output signal from the sensor interface as a generator-recorder.

The optional temperature sensor 926 determines the temperature of the sample in the reservoir of the test sensor 904. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 928 may be a magnetic, optical, or semiconductor memory, another storage device, or the like. The storage medium 928 may be a fixed memory device, a removable memory device, such as a memory card, remotely accessed, or the like.

The processor 922 implements the analyte analysis and data treatment using computer readable software code and data stored in the storage medium 928. The processor 922 may start the analyte analysis in response to the presence of the test sensor 904 at the sensor interface 918, the application of a sample to the test sensor 904, in response to user input, or the like. The processor 922 directs the signal generator 924 to provide the electrical input signal to the sensor interface 918. The processor 922 may receive the sample temperature from the optional temperature sensor 926. The processor 922 receives the output signal from the sensor interface 918. The output signal is generated in response to the redox reaction of the analyte in the reservoir 908.

The processor 922 preferably measures the output signal to obtain a current value from an excitation where the initial current value is greater than those that follow in the decay and within less than about 3 seconds of introducing the sample to the test sensor 904. More preferably, the processor 922 measures the output signal to obtain a current value within less than about 3 seconds of introducing the sample to the test sensor in 904 and obtains the first current value recorded from an excitation where the current values that follow the first current value continuously decrease. Even more preferably, the processor 922 measures the output signal to obtain a current value within less than about 3 seconds of introducing the sample to the test sensor in 904, to obtain the first current value recorded from an excitation where the current values that follow the first current value continuously decrease, and to obtain a current value during the maximum kinetic performance of the test sensor.

The one or more obtained current value is correlated with the analyte concentration of the sample using one or more correlation equations in the processor 922. The results of the analyte analysis may be output to the display 920 and may be stored in the storage medium 928. Preferably, the results of the analyte analysis are output to the display 920 within five seconds or less of introducing the sample to the test sensor, more preferably the results are output to the display 920 within three seconds or less of introducing the sample to the test sensor.

The correlation equations relating analyte concentrations and output current values may be represented graphically, mathematically, a combination thereof, or the like. The correlation equations may be represented by a program number (PNA) table, another look-up table, or the like that is stored in the storage medium 928. Instructions regarding implementation of the analyte analysis may be provided by the computer readable software code stored in the storage medium 928. The code may be object code or any other code describing or controlling the functionality described herein. The data from the analyte analysis may be subjected to one or more data treatments, including the determination of decay rates, K constants, ratios, and the like in the processor 922.

The sensor interface 918 has contacts that connect or electrically communicate with the conductors 909 in the sample interface 914 of the test sensor 904. The sensor interface 918 transmits the electrical input signal from the signal generator 924 through the contacts to the conductors 909 in the sample interface 914. The sensor interface 918 also transmits the output signal from the sample through the contacts to the processor 922 and/or signal generator 924.

The display 920 may be analog or digital. The display may be a LCD adapted to display a numerical reading.

In use, a sample for analysis is transferred into the reservoir 908 by introducing the sample to the opening 912. The sample flows through the channel 910, filling the reservoir 908 while expelling the previously contained air. The sample chemically reacts with the reagents deposited in the channel 910 and/or reservoir 908. Preferably, the sample is a fluid, more preferably, a liquid.

The test sensor 904 is disposed adjacent to the measurement device 902. Adjacent includes positions where the sample interface 914 is in electrical communication with the sensor interface 918. Electrical communication includes wired or wireless transfer of input and/or output signals between contacts in the sensor interface 918 and conductors 909 in the sample interface 914.

While various embodiments of the invention have been described, it will be apparent to those of ordinary skill in the art that other embodiments and implementations are possible within the scope of the invention.

What is claimed is:

1. A biosensor system, for determining the concentration of an analyte in a sample, comprising:
    a reaction means for selectively performing a redox reaction of an analyte,
        where the reaction means comprises a binder, a buffer salt, a mediator comprising at most 20% (w/w) of an inorganic, non-transition metal salt, an enzyme system, and a non-ionic, sugar-based surfactant; and
    a measurement means for measuring a rate of the redox reaction of the analyte,
        where the measurement means comprises at least two conductors;
    where the measurement means measures an output signal value from the reaction means at a maximum kinetic performance within at most 7 seconds of introducing a sample to the reaction means, where the output signal value is responsive to the concentration of the analyte in the sample,
    the measurement means is capable of determining at least one slope deviation of the correlation between analyte concentrations and output current values determined from one or more error parameters responsive to at least one error parameter, and
    the measurement means is capable of determining the analyte concentration in the sample from a compensation equation including at least one reference correlation and the at least one slope deviation of the correlation between analyte concentrations and output current values determined from one or more error parameters;
    where the compensation equation has a $R^2$ value of at least 0.5.

2. The system of claim 1, where the reaction means comprises a reagent composition having an average reagent composition surface area and comprising:
    the binder,
    the buffer salt, present in the reagent composition at a concentration of at most 9.54 nmol per $mm^2$ of the reagent composition surface area,
    the mediator, present in the reagent composition at a concentration of at most 4.76 nmol per $mm^2$ of the reagent composition surface area,
    the enzyme system, and
    the non-ionic surfactant.

3. The system of claim 2, where the reagent composition comprises:
    from about 0.14 to about 0.43 µg of the binder per $mm^2$ of the reagent composition surface area,
    from about 2.30 to 9.54 nmol of the buffer salt per $mm^2$ of the reagent composition surface area,
    from about 1.70 to 4.76 nmol of the mediator per $mm^2$ of the reagent composition surface area,
    from about 0.07 to about 0.3 Units of the enzyme system per $mm^2$ of the reagent composition surface area,
    and from about 0.04 to about 0.24 µg of the non-ionic surfactant per $mm^2$ of the reagent composition surface area.

4. The system of claim 3, where the reagent composition comprises:
    from about 3.40 to about 4.77 nmol of the buffer salt per $mm^2$ of the reagent composition surface area, and
    from about 2.80 to about 4.00 nmol of the mediator per $mm^2$ of the reagent composition surface area.

5. The system of claim 2, where the reagent composition further comprises from about 3 to about 16 ng of an anionic surfactant per $mm^2$ of the reagent composition surface area.

6. The system of claim 1, where the reaction means comprises:
    a reservoir having a reservoir volume,
    at least two conductors in the reservoir, where one of the conductors is a working electrode, and
    a reagent composition disposed on or near the working electrode;
    where the reagent composition comprises:
        the binder,
        the buffer salt, present in the reagent composition at a concentration of at most 67 nmol per µL of the reservoir volume,
        the mediator, present in the reagent composition at a concentration of at most 40 nmol per µL of the reservoir volume,
        the enzyme system, and
        the non-ionic surfactant.

7. The system of claim 6, where the reagent composition comprises:
from about 1 to about 3 μg of the polymeric binder per μL of the reservoir volume,
from about 16 to 67 nmol of the buffer salt per μL of the reservoir volume,
from about 12 to 40 nmol of the mediator per μL of the reservoir volume,
from about 0.5 to about 1.8 Units of the enzyme system per μL of the reservoir volume, and
from about 0.3 to about 1.7 μg of the non-ionic surfactant per μL of the reservoir volume.

8. The system of claim 7, where the reagent composition comprises:
from about 24 to about 34 nmol of the buffer salt per μL of the reservoir volume, and
from about 20 to about 28 nmol of the mediator per μL of the reservoir volume.

9. The system of claim 6, where the reagent composition further comprises from about 20 to about 40 ng of an ionic surfactant per μL of the reservoir volume.

10. The system of claim 1, where the reaction means comprises:
at least two conductors, where one of the conductors is a working electrode having a working electrode area, and
a reagent composition disposed on or near the working electrode;
where the reagent composition comprises:
the binder,
the buffer salt, present in the reagent composition at a concentration of at most 167 nmol per $mm^2$ of the working electrode area,
the mediator, present in the reagent composition at a concentration of at most 100 nmol per $mm^2$ of the working electrode area,
the enzyme system,
a non-ionic surfactant, and
from about 10 to about 350 ng of an ionic surfactant per $mm^2$ of the working electrode area.

11. The system of claim 10, where the reagent composition comprises:
from about 1 to about 7.5 μg of the binder per $mm^2$ of the working electrode area,
from about 16 to 167 nmol of the buffer salt per $mm^2$ of the working electrode area,
from about 12 to 100 nmol of the mediator per $mm^2$ of the working electrode area,
from about 0.5 to about 5 Units of the enzyme system per $mm^2$ of the working electrode area, and
from about 0.3 to about 4.3 μg of the non-ionic surfactant per $mm^2$ of the working electrode area.

12. The system of claim 1, where the reaction means further comprises an ionic surfactant.

13. The system of claim 12, where the ionic surfactant comprises an anionic surfactant.

14. The system of claim 1, where the buffer salt comprises $Na_2HPO_4$.

15. The system of claim 1, where the mediator comprises at most 10% (w/w) inorganic, non-transition metal salt.

16. The system of claim 1, where the mediator comprises at most 5% (w/w) inorganic, non-transition metal salt.

17. The system of claim 1, where the mediator comprises at most 4% (w/w) inorganic, non-transition metal salt.

18. The system of claim 1, where the measurement means measures an output signal value from the reaction means at a maximum kinetic performance within at most 5 seconds of introducing a sample to the reaction means.

19. The system of claim 1, where the measurement means measures an output signal value from the reaction means at a maximum kinetic performance within at most 3.5 seconds of introducing a sample to the reaction means.

20. A test sensor for determining the concentration of an analyte in a sample, comprising:
at least two conductors, where one of the conductors is a working electrode; and
a reagent composition disposed on or near the working electrode, the reagent composition having an average reagent composition surface area and comprising:
a binder,
a buffer salt at a concentration of at most 9.54 nmol per $mm^2$ of the reagent composition surface area,
a mediator at a concentration of at most 4.76 nmol per $mm^2$ of the reagent composition surface area, where the mediator comprises at most 20% (w/w) of an inorganic, non-transition metal salt,
an enzyme system, and
a non-ionic surfactant comprising a sugar-based surfactant.

21. The sensor of claim 20, where the reagent composition comprises
from about 0.14 to about 0.43 μg of the binder per $mm^2$ of the reagent composition surface area,
from about 2.30 to 9.54 nmol of the buffer salt per $mm^2$ of the reagent composition surface area,
from about 1.70 to 4.76 nmol of the mediator per $mm^2$ of the reagent composition surface area,
from about 0.07 to about 0.3 Units of the enzyme system per $mm^2$ of the reagent composition surface area, and
from about 0.04 to about 0.24 μg of the non-ionic surfactant per $mm^2$ of the reagent composition surface area.

22. The sensor of claim 21, where the reagent composition comprises
from about 3.40 to about 4.77 nmol of the buffer salt per $mm^2$ of the reagent composition surface area, and
from about 2.80 to about 4.00 nmol of the mediator per $mm^2$ of the reagent composition surface area.

23. The sensor of claim 20, where the buffer salt comprises $Na_2HPO_4$.

24. The sensor of claim 20, where the mediator comprises at most 5% (w/w) inorganic, non-transition metal salt.

25. A test sensor for determining the concentration of an analyte in a sample, comprising:
a reservoir having a reservoir volume,
at least two conductors in the reservoir, where one of the conductors is a working electrode, and
a reagent composition disposed on or near the working electrode;
where the reagent composition comprises:
a binder,
a buffer salt at a concentration of at most 67 nmol per μL of the reservoir volume,
a mediator at a concentration of at most 40 nmol per μL of the reservoir volume, where the mediator comprises at most 20% (w/w) of an inorganic, non-transition metal salt,
an enzyme system, and
a non-ionic surfactant comprising a sugar-based surfactant.

26. The sensor of claim 25, where the reagent composition comprises
from about 1 to about 3 μg of the binder per μL of the reservoir volume, from about 16 to 67 nmol of the buffer salt per μL of the reservoir volume, from about 12 to 40 nmol of the mediator per μL of the reservoir volume, from about 0.5 to about 1.8 Units of the enzyme system per μL of the reservoir volume, and from about 0.3 to about 1.7 μg of the non-ionic surfactant per μL of the reservoir volume.

27. The sensor of claim 26, where the reagent composition comprises from about 24 to about 34 nmol of the buffer salt per μL of the reservoir volume, and from about 20 to about 28 nmol of the mediator per μL of the reservoir volume.

28. The sensor of claim 25, where the buffer salt comprises $Na_2HPO_4$.

29. The sensor of claim 25, where the mediator comprises at most 5% (w/w) inorganic, non-transition metal salt.

30. A test sensor for determining the concentration of an analyte in a sample, comprising:

at least two conductors, where one of the conductors is a working electrode having a working electrode area; and a reagent composition disposed on or near the working electrode, the reagent composition comprising:

a binder, a buffer salt at a concentration of at most 167 nmol per $mm^2$ of the working electrode area, a mediator at a concentration of at most 100 nmol per $mm^2$ of the working electrode area, where the mediator comprises at most 20% (w/w) of an inorganic, non-transition metal salt, an enzyme system, and a non-ionic surfactant comprising a sugar-based surfactant.

31. The sensor of claim 30, comprising from about 1 to about 7.5 μg of the binder per $mm^2$ of the working electrode area, from about 16 to 167 nmol of the buffer salt per $mm^2$ of the working electrode area, from about 12 to 100 nmol of the mediator per $mm^2$ of the working electrode area, from about 0.5 to about 5 Units of the enzyme system per $mm^2$ of the working electrode area, and from about 0.3 to about 4.3 μg of the non-ionic surfactant per $mm^2$ of the working electrode area.

32. The sensor of claim 31, comprising from about 24 to about 84 nmol of the buffer salt per $mm^2$ of the working electrode area, and from about 20 to about 70 nmol of the mediator per $mm^2$ of the working electrode area.

33. The sensor of claim 30, where the buffer salt comprises $Na_2HPO_4$.

34. The sensor of claim 30, where the mediator comprises at most 5% (w/w) inorganic, non-transition metal salt.

35. A test sensor for determining the concentration of an analyte in a sample, comprising:

at least two conductors, where one of the conductors is a working electrode; and a reagent composition disposed on or near the working electrode, the reagent composition having an average reagent composition surface area and comprising:

a binder, a buffer salt at a concentration of at most 9.54 nmol per $mm^2$ of the reagent composition surface area, a mediator at a concentration of at most 4.76 nmol per $mm^2$ of the reagent composition surface area, where the mediator comprises at most 20% (w/w) of an inorganic, non-transition metal salt, an enzyme system, a non-ionic surfactant, and an ionic surfactant.

36. The sensor of claim 35, where the ionic surfactant comprises an anionic surfactant.

37. The sensor of claim 36, where the reagent composition comprises from about 3 to about 16 ng of the anionic surfactant per mm2 of the reagent composition surface area.

38. A test sensor for determining the concentration of an analyte in a sample, comprising:

a reservoir having a reservoir volume, at least two conductors in the reservoir, where one of the conductors is a working electrode, and a reagent composition disposed on or near the working electrode;

where the reagent composition comprises:

a binder, a buffer salt at a concentration of at most 67 nmol per μL of the reservoir volume, a mediator at a concentration of at most 40 nmol per μL of the reservoir volume, where the mediator comprises at most 20% (w/w) of an inorganic, non-transition metal salt, an enzyme system, a non-ionic surfactant, and an ionic surfactant.

39. The sensor of claim 38, where the ionic surfactant comprises an anionic surfactant.

40. The sensor of claim 39, where the reagent composition comprises from about 20 to about 40 ng of the ionic surfactant per μL of the reservoir volume.

41. A test sensor for determining the concentration of an analyte in a sample, comprising:

at least two conductors, where one of the conductors is a working electrode having a working electrode area; and a reagent composition disposed on or near the working electrode, the reagent composition comprising:

a binder, a buffer salt at a concentration of at most 167 nmol per $mm^2$ of the working electrode area, a mediator at a concentration of at most 100 nmol per $mm^2$ of the working electrode area, where the mediator comprises at most 20% (w/w) of an inorganic, non-transition metal salt, an enzyme system, a non-ionic surfactant, and an ionic surfactant.

42. The sensor of claim 41, where the ionic surfactant comprises an anionic surfactant.

43. The sensor of claim 42, where the reagent composition comprises from about 10 to about 350 ng of the ionic surfactant per $mm^2$ of the working electrode area.

* * * * *

UNITED STATES PATENT AND TRADEMARK OFFICE
CERTIFICATE OF CORRECTION

PATENT NO. : 8,871,069 B2  
APPLICATION NO. : 13/154088  
DATED : October 28, 2014  
INVENTOR(S) : Amy H Chu, Huan-Ping Wu and Boru Zhu Page 1 of 1

It is certified that error appears in the above-identified patent and that said Letters Patent is hereby corrected as shown below:

IN THE CLAIMS

In Column 28, Line 37, in Claim 3, delete "Units" and insert -- units --, therefor.  
In Column 29, Line 9, in Claim 7, delete "Units" and insert -- units --, therefor.  
In Column 29, Line 48, in Claim 11, delete "Units" and insert -- units --, therefor.  
In Column 31, Line 42, in Claim 31, delete "Units" and insert -- units --, therefor.  
In Column 32, Line 15, in Claim 37, delete "mm2" and insert -- $mm^2$ --, therefor.

Signed and Sealed this  
Nineteenth Day of May, 2015

Michelle K. Lee  
*Director of the United States Patent and Trademark Office*